US012431235B1

(12) United States Patent
Serrao et al.

(10) Patent No.: US 12,431,235 B1
(45) Date of Patent: Sep. 30, 2025

(54) AUTOMATIC IDENTIFICATION OF, AND RESPONDING TO, COGNITION IMPAIRMENT

(71) Applicant: UIPCO, LLC, San Antonio, TX (US)

(72) Inventors: Nolan Serrao, Plano, TX (US); Keegan Patrick Hayes, Whitestown, IN (US); Arthur Quentin Smith, Fredericksburg, TX (US); John Andrew Weems, San Antonio, TX (US); Salvador Adrian Bretado, San Antonio, TX (US); Justin Royell Nash, Little Elm, TX (US); David Joaquin Harris, San Antonio, TX (US); Carol Lyn Lawrence, Fair Oaks Ranch, TX (US); Theresa Marie Matowitz, San Antonio, TX (US); Courtney St. Martin, Duluth, GA (US)

(73) Assignee: United Services Automobile Association (USAA), San Antonio, TX (US)

( * ) Notice: Subject to any disclaimer, the term of this patent is extended or adjusted under 35 U.S.C. 154(b) by 473 days.

(21) Appl. No.: 17/558,312

(22) Filed: Dec. 21, 2021

(51) Int. Cl.
*G16H 20/70* (2018.01)
*G06F 9/451* (2018.01)
*G16H 50/20* (2018.01)

(52) U.S. Cl.
CPC ............. *G16H 20/70* (2018.01); *G06F 9/453* (2018.02); *G16H 50/20* (2018.01)

(58) Field of Classification Search
CPC ......... G16H 20/70; G16H 50/20; G06F 9/453
(Continued)

(56) References Cited

U.S. PATENT DOCUMENTS 9,009,156 B1  4/2015  Jiang et al.
9,667,577 B2  5/2017  Deluca et al.
(Continued)

FOREIGN PATENT DOCUMENTS

CN      110414557 A   *   11/2019

OTHER PUBLICATIONS

Williams,P.A.,Jenkins,J.,Valacich,J.,&Byrd,M.D.(2017). MeasuringactualbehaviorsinHCIresearch-acalltoactionandanexample. AISTransactionsonHuman-ComputerInteraction,9(4),339-352. (Year: 2017).*

(Continued)

*Primary Examiner* — Mamon Obeid
*Assistant Examiner* — Winston Furtado
(74) *Attorney, Agent, or Firm* — Potomac Law Group, PLLC; Dannon G. Allbee

(57) ABSTRACT

Aspects of the present disclosure are directed to a cognition analysis and response system that can A) identify and classify machine learning training data and use the training data to build a cognitive impairment machine learning model; B) identify cognitive impairments by applying the cognitive impairment machine learning model and performing a false positive/false negative analysis; and C) apply various automated adaptive measures for users with identified cognitive impairment. The cognition analysis and response system can generate training data by using an unsupervised training process and verifying results with validations of training items that have been pre-classified. The cognition analysis and response system can then iterate through each set of inputs paired with cognitive impairment classification, applying a machine learning model and updating the model based on a comparison of the model output to the cognitive impairment classification.

18 Claims, 15 Drawing Sheets

(58) Field of Classification Search
USPC .......................................................... 705/2
See application file for complete search history.

(56) References Cited

U.S. PATENT DOCUMENTS

| | | | |
|---|---|---|---|
| 10,354,201 | B1 | 7/2019 | Roy et al. |
| 10,594,648 | B2 | 3/2020 | Iyer et al. |
| 2002/0156799 | A1 | 10/2002 | Markel et al. |
| 2003/0046401 | A1 | 3/2003 | Abbott et al. |
| 2006/0256950 | A1 | 11/2006 | Patel et al. |
| 2010/0268682 | A1 | 10/2010 | Lewis et al. |
| 2013/0073949 | A1 | 3/2013 | Barrell et al. |
| 2013/0246904 | A1 | 9/2013 | Seliger et al. |
| 2014/0356824 | A1 | 12/2014 | Dozier |
| 2015/0262016 | A1 | 9/2015 | Rothblatt |
| 2016/0253910 | A1 | 9/2016 | Fisher |
| 2017/0164029 | A1 | 6/2017 | Dey et al. |
| 2017/0371411 | A1 | 12/2017 | Vinmani et al. |
| 2018/0172694 | A1 | 6/2018 | Farokhzad et al. |
| 2018/0176168 | A1 | 6/2018 | Tsou |
| 2018/0356887 | A1 | 12/2018 | Ramaprakash et al. |
| 2019/0020687 | A1 | 1/2019 | Noon et al. |
| 2019/0130436 | A1 | 5/2019 | Ma et al. |
| 2019/0197479 | A1 | 6/2019 | Huang et al. |
| 2019/0333629 | A1 | 10/2019 | Torres |
| 2020/0012665 | A1 | 1/2020 | Das et al. |
| 2020/0137347 | A1 | 4/2020 | Rechner et al. |
| 2020/0372079 | A1 | 11/2020 | De Vries et al. |
| 2021/0098110 | A1 | 4/2021 | Periyasamy et al. |
| 2021/0110895 | A1* | 4/2021 | Shriberg ................. G06F 40/20 |
| 2021/0133509 | A1* | 5/2021 | Wall ...................... G06F 18/285 |
| 2021/0169417 | A1 | 6/2021 | Burton |
| 2021/0228079 | A1 | 7/2021 | Betrouni et al. |
| 2021/0280296 | A1 | 9/2021 | Houy |
| 2021/0304867 | A1 | 9/2021 | Brewer et al. |
| 2021/0343384 | A1 | 11/2021 | Purushothaman et al. |
| 2021/0391048 | A1 | 12/2021 | De Vries et al. |
| 2022/0078197 | A1 | 3/2022 | Jakobsson et al. |
| 2022/0084310 | A1* | 3/2022 | Thyagharajan ...... G06V 10/774 |
| 2022/0084438 | A1 | 3/2022 | Bansal et al. |
| 2022/0116736 | A1 | 4/2022 | Williams et al. |
| 2023/0083418 | A1 | 3/2023 | Mcduff et al. |
| 2023/0096357 | A1 | 3/2023 | Dorn et al. |

OTHER PUBLICATIONS

Tsai, C. F., Chen, C. C., Wu, E. H. K., Chung, C. R., Huang, C. Y., Tsai, P. Y., & Yeh, S. C. (2021). A machine-learning-based assessment method for early-stage neurocognitive impairment by an immersive virtual supermarket. IEEE Transactions on Neural Systems and Rehabilitation Engineering. (Year: 2021).*

Akhter et al., "Conceptual Framework: How to Engineer Online Trust for Disabled Users", Sep. 2009, IEEE, 2009 IEEE/WIC/ACM International Conference on Web Intelligence and Intelligent Agent Technology—Workshops, p. 614-617 (Year: 2009).

Williams et al., "Measuring actual behaviors in HCI research-a call to action and an example", AIS Transactions on Human-Computer Interaction, 9(4), 339-352, Dec. 2017.

* cited by examiner

Support Services for Spouses of Stroke Victims ~1144

Support Groups in Austin, TX: ~1146
  Families of Stroke Victims, Monday & Friday – 6:00 pm: link
  Dealing with Stroke, Tuesday & Thursday – 3:00 pm: link

Counseling Services: ~1148
  Trauma Counseling Specialists: link
  Family Counseling Services: link

Information Resources: ~1150
  What to Expect Following a Stroke: <download>
  Home Setup and Care Recommendations Following a Stroke: <download>

Insurance Services: ~1152
  Review and Update Health Insurance: link
  Review and Update Personal Property Insurance: link
  Review and Update Home Insurance: link

*FIG. 11B*

AUTOMATIC IDENTIFICATION OF, AND RESPONDING TO, COGNITION IMPAIRMENT

CROSS-REFERENCE TO RELATED APPLICATIONS

This application is related to U.S. patent application Ser. No. 17/558,333, titled "Automatic Identification of, and Responding to, Cognition Impairment," filed Dec. 21, 2021, and U.S. patent application Ser. No. 17/558,347, titled "Automatic Identification of, and Responding to, Cognition Impairment," filed Dec. 21, 2021, and which are each herein incorporated by reference in their entirety.

TECHNICAL FIELD

The present disclosure is directed to processes for automatically analyzing user interactions with computing systems to identify users with a cognition impairment and automated actions for assisting such users.

BACKGROUND

About one in three people will develop Alzheimer's disease in their lifetime. Many more people will be affected by other forms of cognition impairment such as brain injury, a learning disability, a stroke, post-traumatic stress disorder (PTSD), depression, schizophrenia, etc. People with such cognition impairments may have a difficult time, for example, focusing their attention, remembering details, recalling what their intentions were or what actions they have already taken, performing a sequence of steps, or interacting with small user interfaces. However, these mental capabilities are assumed of users for many user interfaces. Further, computing systems interfaces have become integrated into nearly every human activity. Everything from driving our cars to sharing photos with friends occurs with at least some interaction with computing systems.

While some computing systems have options to, e.g., manually enable larger controls (icons, text, images, etc.), such accommodations are infrequent, insufficient to allow impaired users to interact with the computing system, require overt action instead of making passive adjustments, and their enablement typically requires greater understanding of the computing system and mental abilities beyond such impaired users. Thus, impaired users are often and unacceptably left out of the everyday activities other people enjoy.

BRIEF DESCRIPTION OF THE DRAWINGS

FIG. 11B is a conceptual diagram illustrating an example of information sources for users identified to be related to a user determined to have a cognitive impairment.

The techniques introduced here may be better understood by referring to the following Detailed Description in conjunction with the accompanying drawings, in which like reference numerals indicate identical or functionally similar elements.

DETAILED DESCRIPTION

Figure 1:
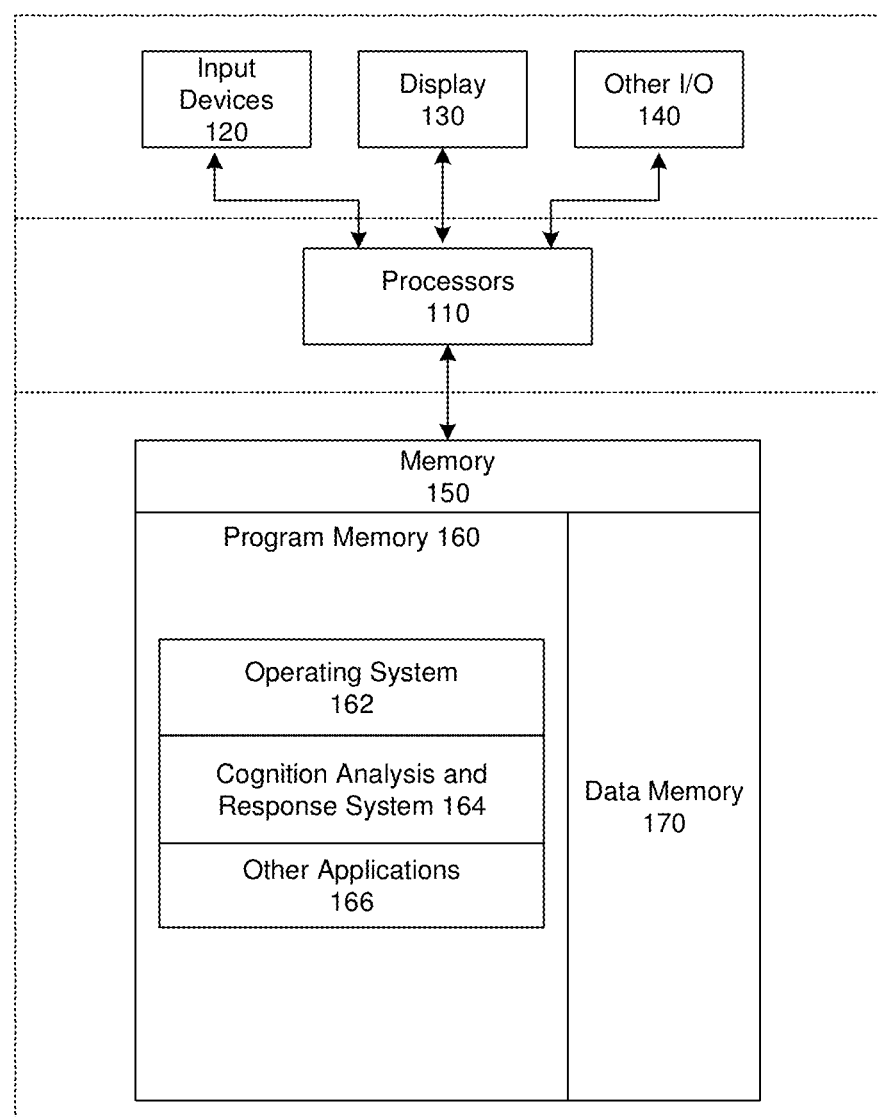
FIG. 1 is a block diagram illustrating an overview of devices on which some implementations can operate.

Aspects of the present disclosure are directed to a cognition analysis and response system that can A) identify and classify machine learning training data by clustering users and extrapolating cognitive impairment identifiers; B) use the training data to build a cognitive impairment machine learning model; C) apply the cognitive impairment machine learning model to inputs for users to identify cognitive impairments, with false positive/false negative corrections; and D) apply various automated adaptive measures for users with identified cognitive impairments.

The cognition analysis and response system can identify and classify machine learning training data by obtaining a set of inputs, in multiple dimensions, for each of multiple users. As discussed in greater detail below, there are multiple data sources that can be used for the multiple dimensions, linked to a particular user, such as user communication history, payment history, a log of errors or lost data, a log of corrective actions, a log of retries or resets, unusual repetitive UI navigation actions, location history, traffic violations, computer user interface (UI) interaction patterns, call center interface interaction patterns, credit card or purchase history, body state/movement records, etc. Based on user volunteered data, public records, acquired data from data suppliers, social media data, insurance claims (e.g., Health and Property and Casualty), and/or anonymized medical data, some of the users for which each set of inputs is obtained can be associated with a cognitive impairment or non-cognitive impairment label. The cognition analysis and response system can apply each set of inputs to an unsupervised machine learning model (e.g., hierarchical clustering, k-means, unsupervised neural network, etc.) which can cluster the users. The cognition analysis and response system can then determine whether a given cluster, with a threshold amount of users with cognitive impairment/non-cognitive impairment labels, has a sufficiently homogeneous set of users with prior-assigned cognitive impairment or non-cognitive impairment labels. When the clusters do not meet these criteria, the cognition analysis and response system can repeat the classification process using different subsets of the multiple dimensions until the resulting clusters meet these criteria. When the clusters meet these criteria, the previous unlabeled users in that cluster can be assigned the cognitive impairment or non-cognitive impairment label for which that cluster was identified to have a sufficiently homogeneous amount of labeled users.

The labels applied to the users through the above classification process can then be part of the training data used by the cognition analysis and response system to build a cognitive impairment machine learning model implementing a supervised learning process. The cognition analysis and response system can accomplish this by iterating through each set of inputs paired to a user (now with a cognitive impairment classification). In each iteration, the cognition analysis and response system can process the dimensions used in the classification as an input to a machine learning model, compare the result to the cognitive impairment classification for the corresponding user, and update the machine learning model parameters based on the comparison (e.g., by applying a loss function), optimizing the model. When the cognition analysis and response system has iterated through all the sets of inputs, the machine learning model is trained to perform cognitive impairment determinations for users not in the training data.

The cognition analysis and response system can apply the cognitive impairment machine learning model, trained as discussed above, to inputs for users to identify potential cognitive impairment. The result from applying the cognitive impairment machine learning model can be a designation of whether the user is experiencing cognitive impairment, and in some cases, an estimation of a type of cognitive impairment. The cognition analysis and response system can also temper these results with a process for identifying false positive and false negative cognitive impairment determinations. The a process for identifying false positive and false negative cognitive impairment determinations can include one or more of: comparing a confidence value from the cognitive impairment machine learning model to a threshold value (e.g., an initial value selected by the model creator), comparing a progression of cognitive impairment determinations over time to one or more patterns of typical patterns of cognitive impairment progression to determine if a current cognitive impairment determination is an anomaly, and/or comparing the cognitive impairment machine learning model inputs to external factors to determine if particular inputs, or the result as a whole, should be excluded from consideration. Depending on the result of this analysis, the cognition analysis and response system can: improve confidence in the cognitive impairment machine learning model result, invalidate the cognitive impairment machine learning model result, or exclude or apply weighting factors to certain inputs used in generating the cognitive impairment machine learning model result and then reapply the cognitive impairment machine learning model.

When a user has been identified as likely having a cognitive impairment, the cognition analysis and response system can apply various automated adaptive measures. In a first embodiment of applying automated adaptive measures, the cognition analysis and response system can update computing system touchpoints and navigation methods to accommodate the cognitive impairment. This can take a variety of forms including one or more of: enabling options to easily connect to a live support specialist or to skip call center menu options; disabling user interfaces and functionality tagged as being more complicated or those identified as less used by the current user; disabling triggering content items; adjusting criteria for recognition of haptic motions like swipes up/down, swipes left/right, double taps, etc.; enabling additional automated explanation and help functions; enabling simpler user interfaces that employ more pictures and less detailed wording; turning off potentially confusing advertising or marketing materials; enabling "quick exit" controls to more easily return to familiar user interfaces; implementing changes in interface input modality such as switching to a voice input; enabling heightened checks for fraud or mistakes for vulnerable users, etc.

In a second embodiment of applying automated adaptive measures, the cognition analysis and response system can provide an enhanced memory system allowing users affected by cognitive impairment to get context-relevant reminders. The cognition analysis and response system can provide this enhanced memory system by enabling a user interface notation system through which users can add comments or reminders to particular user interface elements. In some cases, the cognition analysis and response system can provide suggestions as to which UI elements a notation may be beneficial, such as a payment interface, an interface to elect a service, or an interface that is part of a complicated series of actions. The cognition analysis and response system can then communicate (visual, audible, vibration, etc.) the notation whenever that interface (or a related interface) is provided to the user, which may be in a different system than where the notation was made. For example, a notation made on a UI element through a mobile device application can be surfaced and communicated when a related UI element is displayed on a related website. As another example, a notation made on a UI element through a website can be surfaced to the user or to a call center operator when the user is accessing the call center with a question related to the UI element with the notation. Reminders can include notifications that actions have been missed, or that an action is repetitive and thus unnecessary or undesirable.

In a third embodiment of applying automated adaptive measures, the cognition analysis and response system can automatically provide interfaces for the user or related users to setup cognitive impairment support services. For example, the cognition analysis and response system can identify user trusted members (e.g., family, friends, nurses, etc.) through pre-defined relationships in user profiles and offer cognitive impairment support services, insurance options, guidance in home accommodations/setup, counseling, or support groups. As another example the cognition analysis and response system can provide interfaces for budgeting designed for typical cognitive impairment services, information on public support services for which the user may be eligible, options to specify a financial services representative, power of attorney, or other emergency or alternate contact, etc.

There are some existing systems for testing people for cognitive impairment. These systems tend to require a special application specifically for this process and often use special equipment and may require a neuro specialist. Because these existing systems are specialized for cognitive impairment detection, they require a user to seek out this testing, they do not account for false positives or negatives, and they fail to integrate with other systems to then take automated adaptive measures following a cognitive impairment determination. The systems and methods described herein are expected to overcome these problems with existing systems by providing passive testing for cognitive impairment through logged user interactions. Using a variety of dimensions of such user interactions, the cognition analysis and response system can use methods like bootstrapping data for training a cognitive impairment machine learning model, which can then be used to identify cognitive impairment in users without the users having to take the time or effort to perform targeted cognitive impairment testing. Further, through a system of cognitive impairment machine learning model result analysis, the cognition analysis and response system can determine false positive and false negative results, improving cognitive impairment testing accuracy and applying automated adaptive measures where most appropriate. Finally, the cognition analysis and response system can integrate with multiple computing systems to provide a variety of suggested automated adaptive measures following a cognitive impairment determination.

Several implementations are discussed below in more detail in reference to the figures. FIG. 1 is a block diagram illustrating an overview of devices on which some implementations of the disclosed technology can operate. The devices can comprise hardware components of a device 100 that can automatically analyze user interactions with computing systems to identify users with a cognition impairment and automatically take actions for assisting such users. Device 100 can include one or more input devices 120 that provide input to the Processor(s) 110 (e.g., CPU(s), GPU(s), HPU(s), etc.), notifying it of actions. The actions can be mediated by a hardware controller that interprets the signals received from the input device and communicates the information to the processors 110 using a communication protocol. Input devices 120 include, for example, a mouse, a keyboard, a touchscreen, an infrared sensor, a touchpad, a wearable input device, a camera- or image-based input device, a microphone, or other user input devices.

Processors 110 can be a single processing unit or multiple processing units in a device or distributed across multiple devices. Processors 110 can be coupled to other hardware devices, for example, with the use of a bus, such as a PCI bus or SCSI bus. The processors 110 can communicate with a hardware controller for devices, such as for a display 130. Display 130 can be used to display text and graphics. In some implementations, display 130 provides graphical and textual visual feedback to a user. In some implementations, display 130 includes the input device as part of the display, such as when the input device is a touchscreen or is equipped with an eye direction monitoring system. In some implementations, the display is separate from the input device. Examples of display devices are: an LCD display screen, an LED display screen, a projected, holographic, or augmented reality display (such as a heads-up display device or a head-mounted device), and so on. Other I/O devices 140 can also be coupled to the processor, such as a network card, video card, audio card, USB, firewire or other external device, camera, printer, speakers, CD-ROM drive, DVD drive, disk drive, or Blu-Ray device.

In some implementations, the device 100 also includes a communication device capable of communicating wirelessly or wire-based with a network node. The communication device can communicate with another device or a server through a network using, for example, TCP/IP protocols. Device 100 can utilize the communication device to distribute operations across multiple network devices.

The processors 110 can have access to a memory 150 in a device or distributed across multiple devices. A memory includes one or more of various hardware devices for volatile and non-volatile storage, and can include both read-only and writable memory. For example, a memory can comprise random access memory (RAM), various caches, CPU registers, read-only memory (ROM), and writable non-volatile memory, such as flash memory, hard drives, floppy disks, CDs, DVDs, magnetic storage devices, tape drives, and so forth. A memory is not a propagating signal divorced from underlying hardware; a memory is thus non-transitory. Memory 150 can include program memory 160 that stores programs and software, such as an operating system 162, cognition analysis and response system 164, and other application programs 166. Memory 150 can also include data memory 170, e.g., partially pre-classified training data, cognitive impairment training data classifiers, cognitive impairment machine learning models, historical cognitive impairment patterns and determinations, identifications of external factors implicating cognitive impairment determinations, UI modifications for users identified with cognitive impairments, UI notations and associations between UI elements for cross-system notations, budgeting information, lists of public services, identifications of associations between users, identifications of established agents and advanced directives, configuration data, settings, user options or preferences, etc., which can be provided to the program memory 160 or any element of the device 100.

Some implementations can be operational with numerous other computing system environments or configurations. Examples of computing systems, environments, and/or configurations that may be suitable for use with the technology include, but are not limited to, personal computers, server computers, handheld or laptop devices, cellular telephones, wearable electronics, gaming consoles, tablet devices, multiprocessor systems, microprocessor-based systems, set-top boxes, programmable consumer electronics, network PCs, minicomputers, mainframe computers, distributed computing environments that include any of the above systems or devices, or the like.

Figure 2:
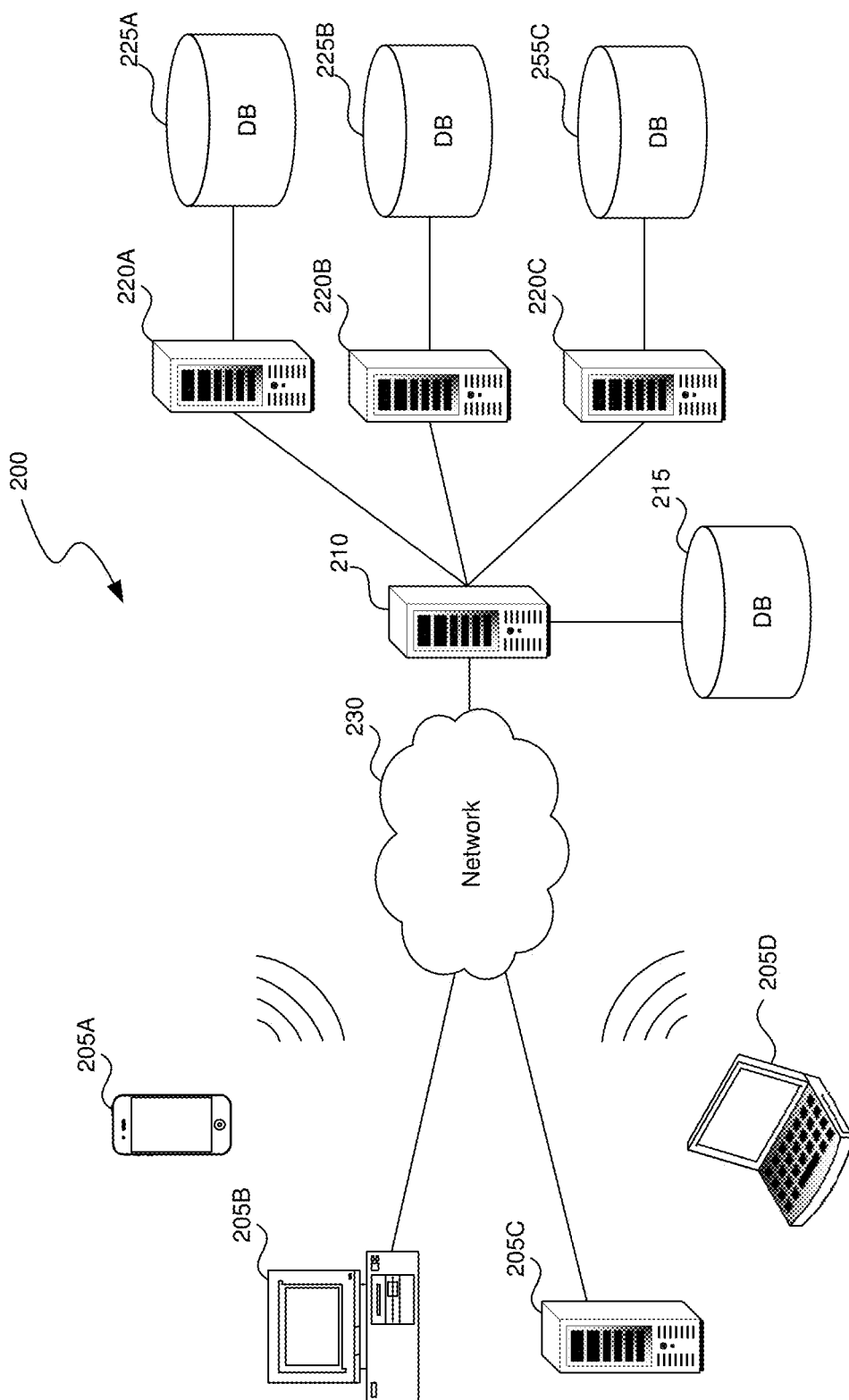
FIG. 2 is a block diagram illustrating an overview of an environment in which some implementations can operate.

FIG. 2 is a block diagram illustrating an overview of an environment 200 in which some implementations of the disclosed technology can operate. Environment 200 can include one or more client computing devices 205A-D, examples of which can include device 100. Client computing devices 205 can operate in a networked environment using logical connections through network 230 to one or more remote computers, such as a server computing device.

In some implementations, server 210 can be an edge server which receives client requests and coordinates fulfillment of those requests through other servers, such as servers 220A-C. Server computing devices 210 and 220 can comprise computing systems, such as device 100. Though each server computing device 210 and 220 is displayed logically as a single server, server computing devices can each be a distributed computing environment encompassing multiple computing devices located at the same or at geographically disparate physical locations. In some implementations, each server 220 corresponds to a group of servers.

Client computing devices 205 and server computing devices 210 and 220 can each act as a server or client to other server/client devices. Server 210 can connect to a database 215. Servers 220A-C can each connect to a corresponding database 225A-C. As discussed above, each server 220 can correspond to a group of servers, and each of these servers can share a database or can have their own database. Databases 215 and 225 can warehouse (e.g., store) information. Though databases 215 and 225 are displayed logically as single units, databases 215 and 225 can each be a distributed computing environment encompassing multiple computing devices, can be located within their corresponding server, or can be located at the same or at geographically disparate physical locations.

Network 230 can be a local area network (LAN) or a wide area network (WAN), but can also be other wired or wireless networks. Network 230 may be the Internet or some other public or private network. Client computing devices 205 can be connected to network 230 through a network interface, such as by wired or wireless communication. While the connections between server 210 and servers 220 are shown as separate connections, these connections can be any kind of local, wide area, wired, or wireless network, including network 230 or a separate public or private network.

Figure 3:
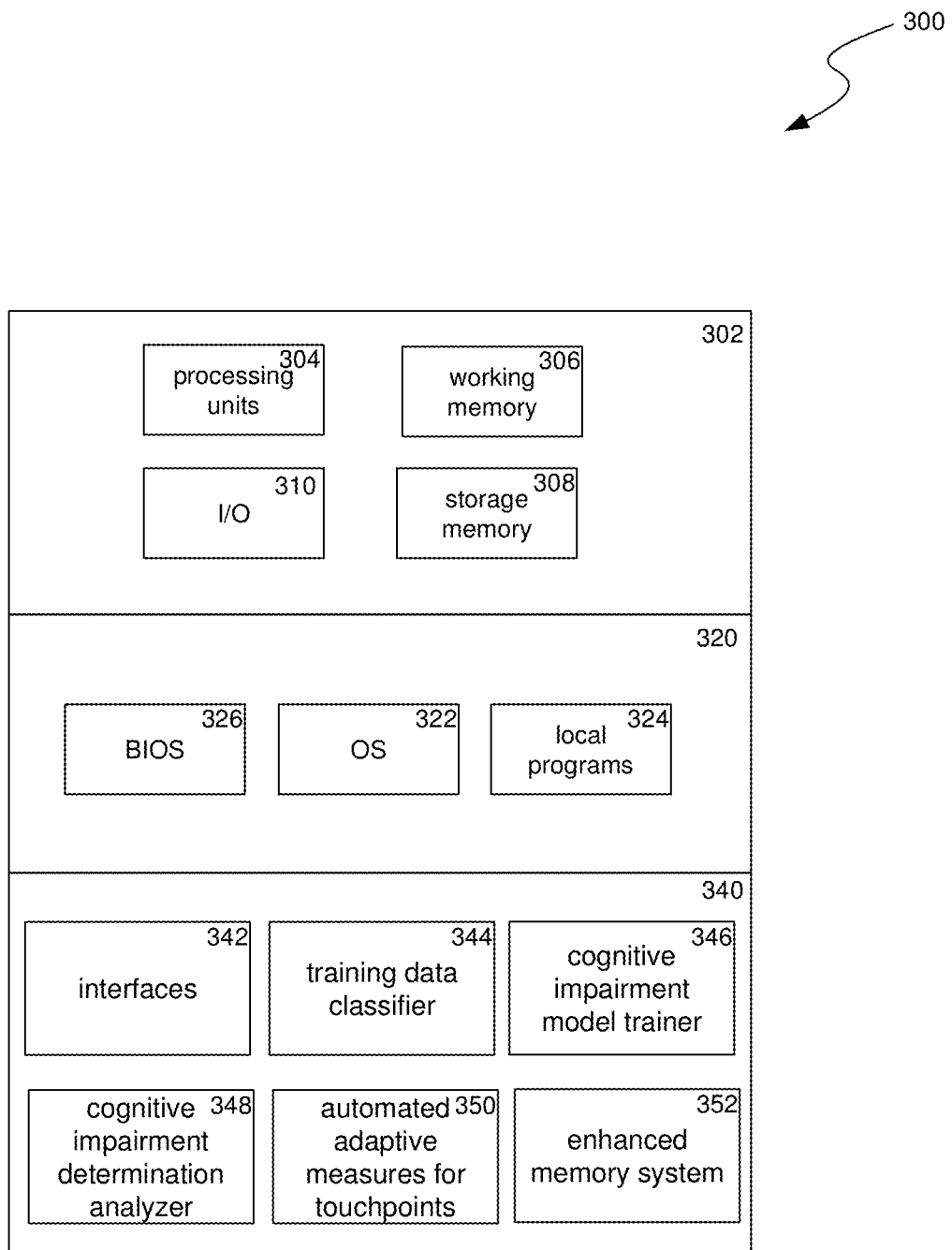
FIG. 3 is a block diagram illustrating components which, in some implementations, can be used in a system employing the disclosed technology.

FIG. 3 is a block diagram illustrating components 300 which, in some implementations, can be used in a system employing the disclosed technology. The components 300 include hardware 302, general software 320, and specialized components 340. As discussed above, a system implementing the disclosed technology can use various hardware including processing units 304 (e.g. CPUs, GPUs, APUs, etc.), working memory 306, storage memory 308 (local storage or as an interface to remote storage, such as storage 215 or 225), and input and output devices 310. In various implementations, storage memory 308 can be one or more of: local devices, interfaces to remote storage devices, or combinations thereof. For example, storage memory 308 can be a set of one or more hard drives (e.g. a redundant array of independent disks (RAID)) accessible through a system bus or can be a cloud storage provider or other network storage accessible via one or more communications networks (e.g. a network accessible storage (NAS) device, such as storage 215 or storage provided through another server 220). Components 300 can be implemented in a client computing device such as client computing devices 205 or on a server computing device, such as server computing device 210 or 220.

General software 320 can include various applications including an operating system 322, local programs 324, and a basic input output system (BIOS) 326. Specialized components 340 can be subcomponents of a general software application 320, such as local programs 324. Specialized components 340 can include training data classifier 344, cognitive impairment model trainer 346, cognitive impairment determination analyzer 348, automated adaptive measures for touchpoints 350, enhanced memory system 352, and components which can be used for providing user interfaces, transferring data, and controlling the specialized components, such as interfaces 342. In some implementations, components 300 can be in a computing system that is distributed across multiple computing devices or can be an interface to a server-based application executing one or more of specialized components 340. Although depicted as separate components, specialized components 340 may be logical or other nonphysical differentiations of functions and/or may be submodules or code-blocks of one or more applications.

The training data classifier 344 can use unsupervised learning to initially classify user data instances as being associated with a user having or not having a cognitive impairment. The training data classifier 344 can then further validate these initial classifications based on some of the user data instances having been pre-classified. Finally, the training data classifier 344 can label each user data instance as being associated with a user having or not having a cognitive impairment, thereby creating training data for cognitive impairment model trainer 346. Additional details on classifying user data instances as being associated with a user having or not having a cognitive impairment, to generate model training data, are provided below in relation to FIG. 4 and FIG. 8.

The cognitive impairment model trainer 346 can receive labeled pairs of A) user data instances and B) labels of the associated user having or not having a cognitive impairment, as training data. The cognitive impairment model trainer 346 can then train a model to recognize cognitive impairment for other user data instances not in the training data set. Additional details on training a machine learning model to perform cognitive impairment estimations are provided below in relation to FIG. 5.

The cognitive impairment determination analyzer 348 can take results from the model trained by cognitive impairment model trainer 346 and put them in terms of a current context to determine whether a particular cognitive impairment determination should be ignored or reevaluated according to historical and contextual factors. This can include determining whether a confidence value for a cognitive impairment estimation is above a threshold level, whether a cognitive impairment estimation matches known cognitive impairment patterns for similar users, and/or determining whether the cognitive impairment is likely to be skewed due to external contextual factors. In some implementations, a combination of results from these analyses can be used to make a final determination to include, exclude, or reevaluate a given cognitive impairment estimation. Additional details on performing false positive and false negative analysist on cognitive impairment estimations are provided below in relation to FIG. 6.

The automated adaptive measures for touchpoints 350 can provide heightened fraud and/or mistake monitoring, can remove content items identified as potentially confusing or triggering, can enable enhanced help services, can provide information for support and services the user and/or related users may be eligible to receive or may find helpful for the identified cognitive impairment, can provide a tool to setup a budget for expected cognitive impairment costs, and/or can provide a tool to setup agents or advanced directives. Additional details on modifying computing system flows and touchpoints based on a cognitive impairment determination are provided below in relation to FIG. 7A, FIG. 7C, FIG. 9, FIG. 11A, FIG. 11B, and FIG. 11C.

The enhanced memory system 352 can provide tools allowing a user to make a notation on any given UI element in a system (e.g., through a website, app, or call center). The UI elements across the systems can have identified relationships, and when a UI element is provided and that provided UI has a notation or is related to another UI element with a notation, that notation can be provided to the user. This can include a notation made in one system (e.g., on a website) appearing in another system (e.g., as an auditory notation in a call center menu). Additional details on providing a notation system that facilitates notations on any arbitrary UI element and persists the notations across computing systems to related UI elements are provided below in relation to FIG. 7B and FIG. 10.

Those skilled in the art will appreciate that the components illustrated in FIGS. 1-3 described above, and in each of the flow diagrams discussed below, may be altered in a variety of ways. For example, the order of the logic may be rearranged, substeps may be performed in parallel, illustrated logic may be omitted, other logic may be included, etc. In some implementations, one or more of the components described above can execute one or more of the processes described below.

Figure 4:
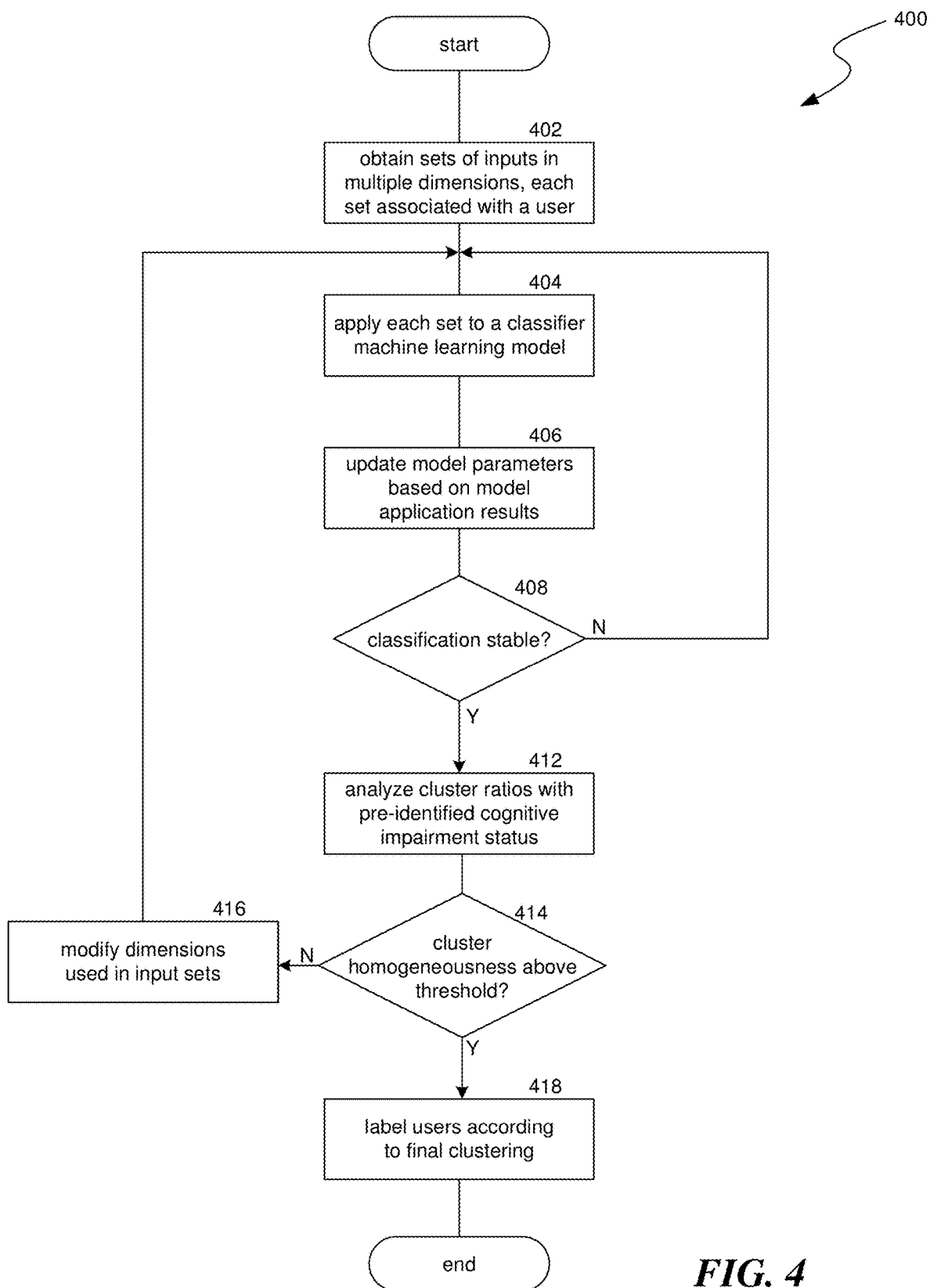
FIG. 4 is a flow diagram illustrating a process used in some implementations for applying unsupervised machine learning to perform user classifications.

FIG. 4 is a flow diagram illustrating a process 400 used in some implementations for applying unsupervised machine learning to perform user classifications. In various implementations, process 400 can be performed on a computing system in response to a user command supplying one or more sources for inputs and an instruction to classify corresponding users.

At block 402, process 400 can obtain sets of inputs in multiple dimensions, each set associated with a user. There are multiple data sources that can be used for the multiple dimensions, linked to a particular user, and process 400 can utilize all or a subset of these sources.

One source of inputs can be from communication histories associated with a user. These can include, for example, logs of text messages, emails, logs from calls to call centers, interactions with chat-bots, etc. In some cases, the communication source inputs can include identifications of variations between communication instances or over time, such as identifications of emotion state changes, language structure changes, word choice changes, etc.

Another source of inputs can be payment history or other transaction history of users. For example, process 400 can gather instances of what was purchased using various accounts, payment history for accounts (e.g., whether payments were missed, whether payments are repeated, and whether such missed or repeated payments is uncharacteristic for a the given user); whether items purchased are in identified categories, (e.g., excessively purchasing items such as locks, fire extinguishers, or weapons that indicate an increase in fear or aggression); whether items purchased are outside an expected range for the given user (e.g., abnormal purchase for the user's location, time of year, etc., that don't align with the user's lifestyle such as buying car parts when the user doesn't own a car, buying a volume of a product that's unusual for the user or type of user, etc.); or whether purchase are from vendors that sell goods or services associated with coping with cognitive impairment.

Yet another source of inputs can be a log of errors or lost data, unnecessarily repeated actions, repeated navigations (swipes as an example). An example of such inputs can be a history of incorrect password attempts, PIN or password reset requests, loss of credit card notices, or detections of fraud (especially when a subsequent fraud check-in results in the user indicating no fraud occurred). In some implementations, these values can be shown as a ratio or other statistical value comparing the user to the user's history of such events or to the typical frequency of such events in other users.

An additional source of inputs can be statistical factors for cognitive impairment. Examples of such statistical factors can include the user's age, lifestyle (e.g., known habits for drinking, using drugs, smoking, etc.), or genetic predisposition factors (e.g., family history or known genetic markers for the user).

In some implementations, further inputs can be a recorded images of the user. For example, a device with a camera facing the user can capture body movement, facial tick, eye movements, etc. These features can be analyzed for indications of cognitive impairment, through explicit mappings of user movement features to cognitive impairment (e.g., looking for loss of mobility in the user's face, hand tremors, loss of motor control, aggressive postures, etc.) or can be supplied to a machine learning model trained to identify such cognitive impairments from sequences of images.

A further source of inputs can be a location or body state history for the user. For example, the location information can include traffic or in-home movement patterns (particularly patterns identified as abnormal, e.g., circling around a place the repeatedly, going from a location and then going back home without stopping, etc.) Traffic violation frequency (as compared to the user's history or to a typical user) can also be used as an input. An example of body state history can include, e.g., facial or gesture recognition to identify emotional states (which may be compared over a period for changes in emotional state over time). Another example of body state history can include features identified from device interactions (e.g., hand pressure or steadiness on an interface, how long buttons are pressed, how many times the user taps the same button multiple times in a row, etc.)

Another source of inputs can be identifications of atypical computer user interface (UI) interaction patterns. Examples of such atypical patterns include a user failing a captcha process an abnormal amount; atypical or slow selections in an automated call center menu system; interactions flagged by a call center representative; frequent missed clicks, page refreshes, or going to a page and then immediately going back; use of atypical language with a chatbot; etc.

A yet further source of inputs can be any of the above sources, with values taken over a period of time (e.g., 6 months, 1 year, 5 years, etc.) and analyzed for cognitive impairment indicia. This analysis can include determining whether these values change significantly over the time period or identifying aberrations of these values as compared to patterns, identified for that input type, for typical users over the time period.

Each of the sets of inputs identified can be associated with a user (e.g., via a user ID), and some of these users can have a cognitive impairment identification (e.g., not having a cognitive impairment or as having a cognitive impairment—or a type of cognitive impairment). In various cases, these cognitive impairment identifications can be based on user volunteered data (or volunteered by a family member—e.g., to for account access of an impaired relative), public records (e.g., cause of death, veteran affairs data, DMV license revocation records, etc.), insurance claims, anonymized medical data, etc.

At block 404, process 400 can apply each set of inputs, each corresponding to a particular user, to an unsupervised machine learning classification model and at block 406, process 400 can update model parameters based on the results of applying the model. For example, each input in a set of inputs for a particular user can be encoded in a value and set in a corresponding slot in a sparse vector for provisioning to the classification model at block 404. Updating the model parameters at block 406 can depend on the type of classification model used, but for example, can include updating a starting cluster center points for a k-means classification. The iteration between blocks 404-408 can repeatedly A) map input sets to a semantic space and grouping to the closest cluster center point, B) update the center points to be in the center of the set of results grouped to that center point, and C) reapply the model to the new center points until, at block 408, process 400 determines that the center points have not moved above a threshold amount (the classification is stable) in the previous iteration of the loop. There are a variety of clustering models that can be applied at blocks 404-408 besides the k-means model described; additional examples include hierarchical clustering and unsupervised neural networks. In general, these models learn to mimic the data they're given, updating model parameters to better predict an input classification.

At block 412, process 400 can identify a statistic (e.g., a ratio), in each cluster, between the users pre-identified in that cluster with a positive cognitive impairment and a negative cognitive impairment. For example, a cluster could have 100,000 and 10,000 of them have a pre-defined cognitive impairment label. Of these 10,000, 9,500 may have a positive cognitive impairment label and 500 may have a negative cognitive impairment label. Thus, in this example, the ratio would be 9,500/500 or 19/1.

At block 414, process 400 can determine if the cluster homogeneousness, as defined by the ratios determined at block 412, are above a threshold. For example, process 400 can determine if the ratio for each cluster is at least 10/1. If so, process 400 can proceed to block 418; if not, process 400 can proceed to block 416. At block 416, process 400 can modify (randomly or in a prescribed manner) the dimensions used in the input sets for the unsupervised classification. Thus, if the resulting classifications do not produce groups of users that have (mostly) the same pre-defined cognitive impairment labels, the classification may have not been sufficiently targeted on cognitive impairment as a classification metric, and thus the types of inputs used in the classification should be modified (in the loop between blocks 404 and 416) until the classification is targeted on cognitive impairment. This modification can include removing or substituting dimensions (i.e., one or more of the sources of data described for block 402). The selection of which dimension to remove or substitute can be based on random selection or on a manual classification of which data sources are most likely to provide accurate cognitive impairment determination (iteratively removing those classified as less likely). In some implementations, at block 416, process 400 can make other modifications to the process, such as by modifying the starting cluster center points for the unsupervised learning process performed in blocks 404-408. In some cases, the loop between blocks 404 and 416 can be performed for all possible combinations of dimensions.

At block 418, process 400 can apply, for each cluster, the cognitive impairment label that is most common for the pre-labeled users in the cluster to the users without a cognitive impairment label in that cluster. In some implementations, where the loop between blocks 404-416 performed multiple iterations, process 400 can use the clustering result that had the highest ratios computed at block 412 or can use the most common cognitive impairment cluster grouping found for each user across the iterations that passed from block 414 to block 418. Process 400 can then return the input sets, now associated with users each labeled with a cognitive impairment or non-cognitive impairment identifier. Process 400 can then end.

Figure 5:
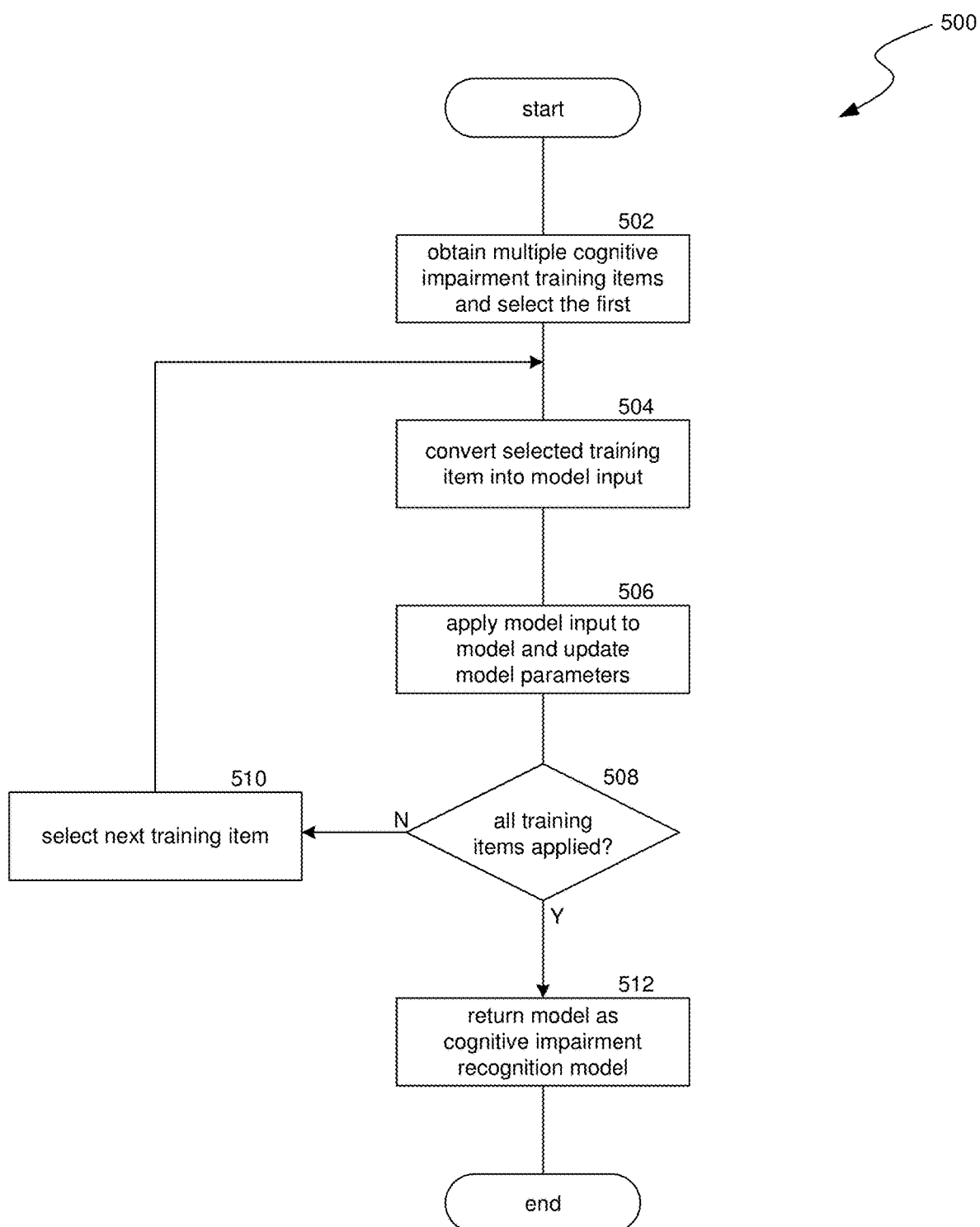
FIG. 5 is a flow diagram illustrating a process used in some implementations for training a cognitive impairment recognition model.

FIG. 5 is a flow diagram illustrating a process 500 used in some implementations for training a cognitive impairment recognition model by implementing a supervised learning process. Process 500 can be performed, e.g., following process 400 or in response to a separate user command supplying training data, generated from process 400 or from another source.

At block 502, process 500 can obtain multiple cognitive impairment training items and can select a first of the training items. In some implementations, the cognitive impairment training items can be the items produced by process 400. Each training item can include one or more inputs (e.g., those outlined above in relation to block 404, which may exclude inputs removed at block 416) and can be associated with a user labeled as either having or not having a cognitive impairment. In some implementations, these cognitive impairment labels can be for a particular type of cognitive impairment (e.g., dementia, brain injury, learning disability, stroke, PTSD, depression, schizophrenia, etc.), as well as for different types of sensory impairments (e.g., hearing, sight, touch, fine motor skills, etc.) allowing the cognitive impairment model produced by process 500 to identify a cognitive impairment type and cognitive impairment impact.

At block 504, process 500 can convert the selected training item into input for a machine learning model. This can include converting the data in each input dimension into one or more values that can be entered in a corresponding slot in a vector, which can be supplied to the machine learning model. For example, the analysis of communication histories can define the identifications of emotional state changes, language structure changes, word choice changes, as corresponding codes; the payment history can include a value representing a number of late payments, a number of repeated payments, or ratios of these to such values for the user in the past or to a typical user; the transaction history can include a frequency that items were purchased indicating a particular emotional state (e.g., fear or aggression) and/or a frequency of purchases atypical for the user or type of user; the log of lost items or data can be encoded as a value indicating a frequency of such losses (e.g., lost password, lost PIN, lost credit card, etc.) as compared to the user's past loss rate or the loss rate for a typical user; statistical factors for cognitive impairment can be encoded as corresponding values; location and body state history can be analyzed for abnormalities (e.g., driving and returning to the start without stopping anywhere, traffic stops, high frequency of aggression or confusion, etc.) and the frequency of such abnormalities can be used as a value in the model input; similarly UI interaction patterns can be analyzed for abnormalities (e.g., failing a captcha process an abnormal amount; atypical or slow selections in an automated call center menu system; frequent missed clicks, etc.) and the frequency of such abnormalities can be used as a value in the model input; etc.

At block 506, process 500 can apply a machine learning model to the model input generated at block 504, can compare the results of the model to the cognitive impairment label assigned to the user associated with that input set and, based on the comparison, can update parameters of the model. For example, the model can be one of various types of neural networks which takes the input through various input nodes, where each node is a function that transforms the input and passes the results, with a particular edge weight, to one or more nodes in a next layer (and in cases to each node in a next layer) of the model, until finally one or more output nodes produce a value that can be mapped to an overall cognitive impairment prediction result. A loss function can then be applied to update the node coefficients and/or edge weights so the output cognitive impairment prediction result of the model is closer to the known cognitive impairment label for the associated user. In other implementations, variety of other machine learning models such as support vector machines, decision trees/forests, etc. can be used instead or in addition to a neural network.

At block 508, process 500 can determine whether all the training items obtained at block 502 have been used in training the model. If not, process 500 can continue to block 510 where a next training item is selected to be applied in the loop between blocks 504 and 510. Once all the training items have been applied, process 500 can continue to block 512 where it can return the model, now trained to predict cognitive impairment status for user input sets not in the training items. Process 500 can then end.

The model produced by process 500 can by utilized to make cognitive impairment predictions for particular users. This can include obtaining inputs for the user, similar to the input from one of the training items of block 502; convert that input into model input, similarly to the conversion performed at block 504; and receive from the model a cognitive impairment prediction for the user. In some cases, the value produced by the model can also be used as a confidence factor, depending on how close the value is to a preferred value. For example, if the model produces a value between zero and one, zero being no cognitive impairment and one being cognitive impairment, the closer the value produced is to one of these values the higher the confidence factor.

Figure 6:
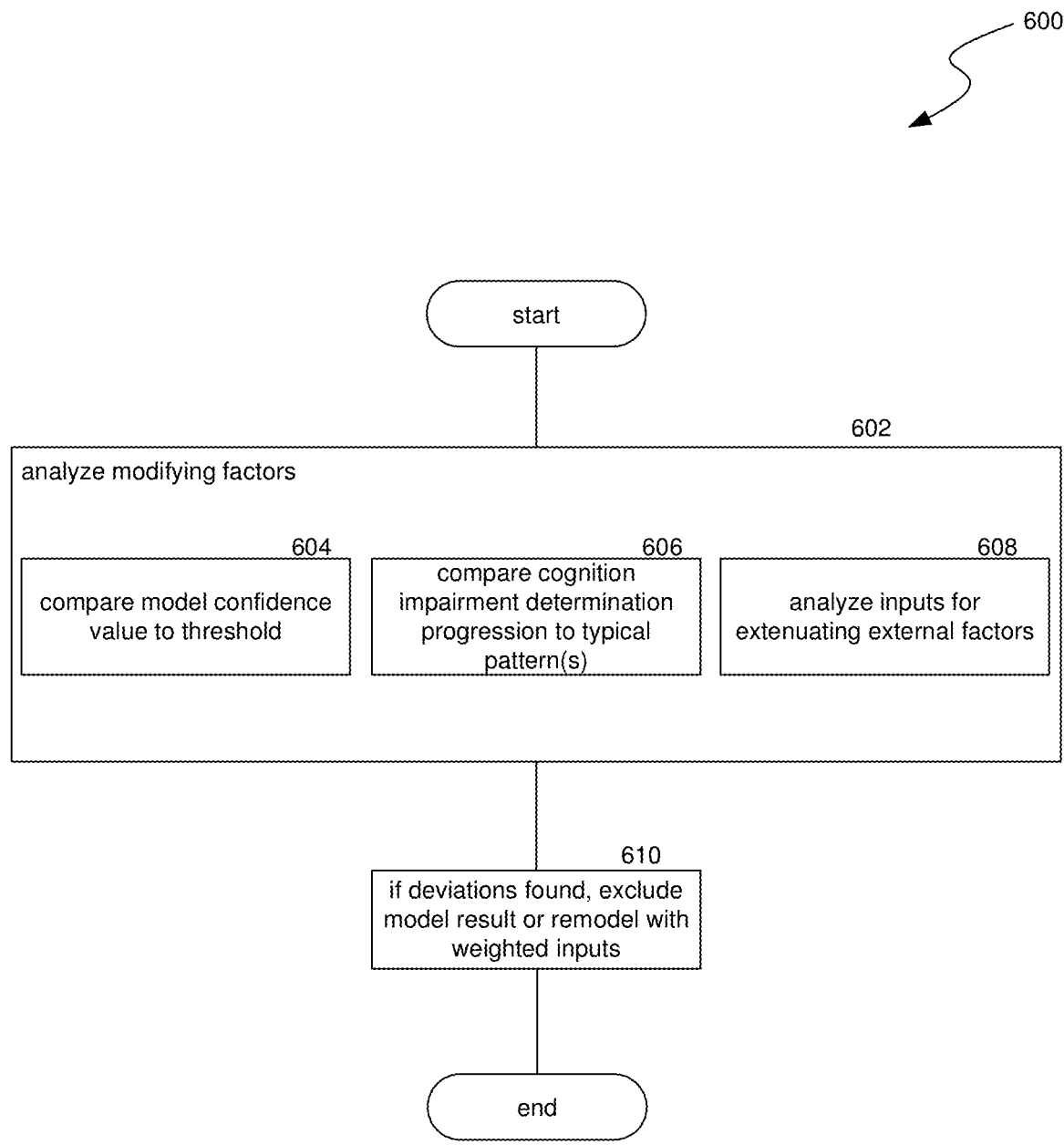
FIG. 6 is a flow diagram illustrating a process used in some implementations for analyzing results of a cognitive impairment recognition ML model for false positives and/or false negatives.

FIG. 6 is a flow diagram illustrating a process 600 used in some implementations for analyzing results of a cognitive impairment recognition machine learning model for false positives and/or false negatives. The model generated by process 500 can be applied to a set of inputs for a particular user to produce a prediction of whether that user likely has a cognitive impairment. Process 600 can be performed following such a cognitive impairment prediction, either automatically or from a user issuing a command to check results from the cognitive impairment prediction model.

At block 602, process 600 can analyze modifying factors that might cause the cognitive impairment prediction model's results to be inaccurate. In various cases, such modifying factors can include an extraordinary event occurring causing inputs to be outside normal ranges, momentary spikes in results that should be ignored, or the model results being inconclusive. Block 602 may perform one or more of blocks 604-608 to make these determinations.

As a first sub-block of block 602, at block 604 process 600 can compare a confidence score produced by the cognitive impairment prediction model to a threshold to determine if the confidence value is sufficient to trust the cognitive impairment prediction. For example, the cognitive impairment prediction model may produce a value between 0 and 1, where a 0 indicates the strongest prediction of no cognitive impairment, a 1 indicates the strongest prediction of cognitive impairment and a 0.5 indicates no cognitive impairment prediction can be determined. At block 604, process 600 can flag the cognitive impairment prediction as unreliable if the prediction is within a range, such as 0.3-0.7, meaning a cognitive impairment prediction is only accepted if the result is greater than or equal to 0.7 and a no cognitive impairment prediction is only accepted if the result is less than or equal to 0.3.

As a second sub-block of block 602, at block 606 process 600 can use a log of cognitive impairment predictions made for the current user over a period of time (e.g., 6 months, 1 year, 5 years, etc.) and compare the results with a pattern.

In some implementations, the pattern can be a typical pattern of cognition impairment predictions for users accurately determined to have a cognitive impairment. In such implementations, if the predicted cognitive impairment determinations in the period of time (e.g., over at least multiple months) are consistently different from the progression of cognitive impairment determinations made for users who have been determined to be accurately labeled, this can signify that the cognitive impairment prediction is not accurate for the current user.

In other implementations, the pattern can be a function fit to the log of previous cognitive impairment predictions for time values, to see if the current prediction is a potential aberration. For example, process 600 can determine whether the cognitive impairment prediction value is within a threshold distance of the y-value of the function for a given x-value that is the time the prediction was made. Thus, if the cognitive impairment prediction value does not closely align to the function fit to the previous cognitive impairment predictions (e.g., over at least multiple months), it can indicate the current prediction is the result of abnormal data and may not be trusted. Thus, the cognitive impairment prediction may only be used when the prediction value is consistently or statistically rising over time—as opposed to a sudden spike in the value of the cognitive prediction.

As a third sub-block of block 602, at block 608 process 600 can analyze whether any of the inputs (or the cognitive impairment prediction as a whole), used in generating the cognitive impairment prediction, may correspond to extenuating external factors that may render their use in cognitive impairment prediction unsuitable. Such extenuating external factors can include, for example, identification of a user as a non-native English speaker as an extenuating factor for the user's communication history; a recent update to a computing system UI or other functionality as an extenuating factor for atypical computer UI interaction patterns; an identified stressor such as a pandemic, an economic change (e.g., stock market dip), election or other political upheaval, holiday season, extreme weather or catastrophe in the area of the user, or the user engaging in stressful activity when the input was recorded (e.g., driving), any of which can be an extenuating factor for any of the inputs or the cognitive impairment result as a whole. Such extenuating factors can be specified by a system administrator or automatically monitored by process 600 from a set of specified sources (e.g., weather providers, news outlets, calendars—e.g., political or holiday calendars—health monitoring organizations, disaster relief organizations, stock market reports, etc.)

At block 610, process 600 can, if the modifying factors analyzed at block 602 show a deviation, take a corrective action. Process 600 can determine that the modifying factors show a deviation when the results from each of block 604, 606, and 608 do not meet a corresponding threshold and/or when a weighted combination of the results from all of the blocks 604, 606, and 608 do not meet another threshold. The weighted combination, for example, can be a weighted average of values produced by each of blocks 604, 606, and 608, where the weights are determined, e.g., by a regression analysis on previously generated cognitive impairment predictions and corresponding accuracy determinations. The corrective action taken at block 610 can be, for example, excluding the cognitive impairment prediction from being used in labeling the user and/or causing the model to re-execute, but excluding or reweighting some of the inputs used by the model for the previous cognitive impairment prediction. Process 600 can then end.

Figure 7A:
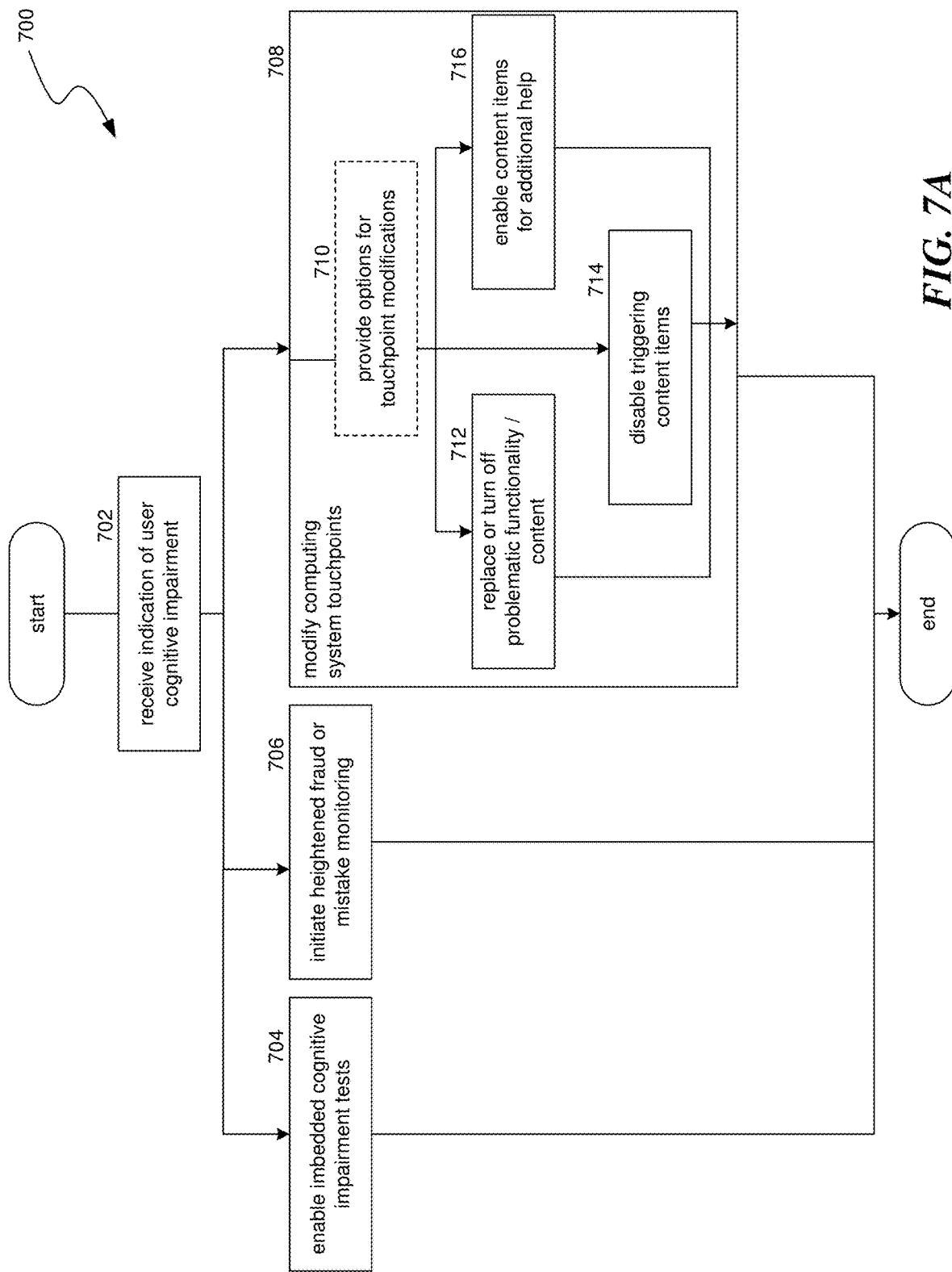
FIGS. 7A-7C are flow diagrams illustrating processes used in some implementations for providing automated adaptive measures for users with identified cognitive impairment.

FIG. 7A is a flow diagram illustrating a process 700 used in some implementations for providing automated responses to identifications of users with cognitive impairment by updating computing system flows and touchpoints. In some cases, process 700 can be performed automatically following a cognitive impairment prediction made by the model produced by process 500 and/or following a validation of the cognitive impairment prediction made by process 600. In other cases, process 700 can be performed in response to a user command or action. In various implementations, process 700 can be performed on a server system, e.g., a server system that hosts a website, provides data for an app, or serves a call center; or process 700 can be performed on a client system (e.g., as JavaScript or other client-side execution; as code to make modifications included as part of an app; etc.)

At block 702, process 700 can receive an indication that a current user has a cognitive impairment. This can be received as the output of the model produced by process 500, which may have been validated as not a false positive by process 600. In some implementations, the cognitive impairment prediction can include a prediction of a type of the cognitive impairment (e.g., dementia, brain injury, a learning disability, a stroke, post-traumatic stress disorder (PTSD), depression, schizophrenia, etc.) and a potential impact of the impairment like limited hearing, sight, tough, motor skills or the like.

In various implementations, process 700 can next perform one or more of blocks 704, 706, or 708. In some implementations, one or more of blocks 704, 706, or 708 can be skipped.

At block 704, process 700 can enable explicit cognitive impairment tests as embedded features in a computing system interface. A number of interaction tests have been developed (e.g., the Montreal Cognitive Assessment (MoCA) and variations on the Clock Drawing Test (CDT), including through MIT research that uses a digital pen to capture time-stamped pen coordinates, allowing analysis of both the resulting drawing and the process used by the subject to draw it, as discussed in http://groups.csail.mit-.edu/mug/pubs/Souillard2015MLJ.pdf) for computing systems that test user reactions for cognitive impairment. By embedding these explicit tests in a website or app interface, process 700 can further verify the received cognitive impairment prediction. The results of such verifications can be used to add to the training data, which can be used to retrain the model by process 500.

At block 706, process 700 can initiate heightened fraud or mistake monitoring. In some cases, this can include adjusting thresholds for existing fraud and mistake checking systems such that activities, which would otherwise not rise to the level of a fraud or mistake determination, trigger such protective measures. In some implementations, this can also or alternatively include setting a flag for the user's account indicating that additional fraud or mistake research should be provided for this user.

At block 708, process 700 can modify computing system touchpoints, such as website UI elements, app components, haptic navigation, call center menus and flows, etc., based on the cognitive impairment indication. While any block can be removed or rearranged in various implementations, block 710 is shown in dashed lines to indicate there are specific instances where block 710 is skipped. At block 710, process 700 can provide the user with options to control which features are replaced or turned off at block 712, which content items to disable at block 714, and/or which help items to enable at block 716. If the user does not select any of the options for a corresponding block, that block can be skipped. In some implementations, where block 710 is not performed, process 700 can select which of these options to take according to A) a default set of options, B) a mapping of cognitive impairment type to options; or C) by initially providing all the options and allowing users to later adjust or make other selections.

At block 712, process 700 can replace or turn off problematic functionality and/or content. Problematic functionality and/or content can include, e.g., functionality tagged (e.g., by an administrator) as complicated, dense, or with interfaces that are more difficult to operate. An example of such modifications includes making menus or a home screen show only the top (e.g., 3-5) used items or the top items most often previously used by this user. Another example of such modifications includes replacing sections of content that display above a threshold amount of words with less words or images, or simpler words and images. Another option is to enable or disable verbal/audible functions based on user cognitive condition. Yet another example of such modifications includes removing unnecessary or potentially confusing features such as advertising or marketing materials, status notifications, design features, etc. A further example of such modifications include changing or enabling an interaction modality, such as by enabling a voice command interface or adding a textual AI assistant.

At block 714, process 700 can disabling triggering content items. These can be content item that are determined to remind a user of a traumatic experience which may be difficult for them given their cognitive impairment. For example, a user identified as suffering from PTSD due to a military deployment may have references to that deployment or deployments in general removed. As another example, a user suffering from a dementia cognitive impairment, and thus who may be confused or angered by references to past communications or other memory dependent interactions, can have such elements removed. Other triggers like visual triggers, such as flashing graphics that induce confusion or seizures can be removed.

At block 716, process 700 can enable content items or features that provide additional help for users identified with cognitive impairment. A first example of such a feature includes a set of guided experiences or walkthroughs for common functions (e.g., providing a sidebar in a website where more detailed instructions and walkthroughs are provided for a currently selected function). A second example of such a feature includes adding a control, accessible from multiple locations in an app or from multiple pages within a website, that will take the user to a more familiar location. For example, a prominent "HOME" button can be added to an app, that is visible to a user from within any widget provided by the app, that takes the user to the home screen of that app (e.g., if the user finds herself interacting with a function that is confusing). A third example of such a feature includes turning on a specific "call me" option on an app or website interface, triggering the system to have a representative call the user. A fourth example of such a feature includes bypassing automated menus in a call center once the user with a cognitive impairment is identified, taking the user to a live representative, bypassing a wait queue at the call center, and/or routing the user to a representative specially trained to interact with users suffering from a cognitive impairment. A fifth example is the enablement of haptic or audible capabilities for navigation, option selection, and the like.

Following the execution of the one or more of block 704, 706, and/or 708, process 700 can end.

Figure 7B:
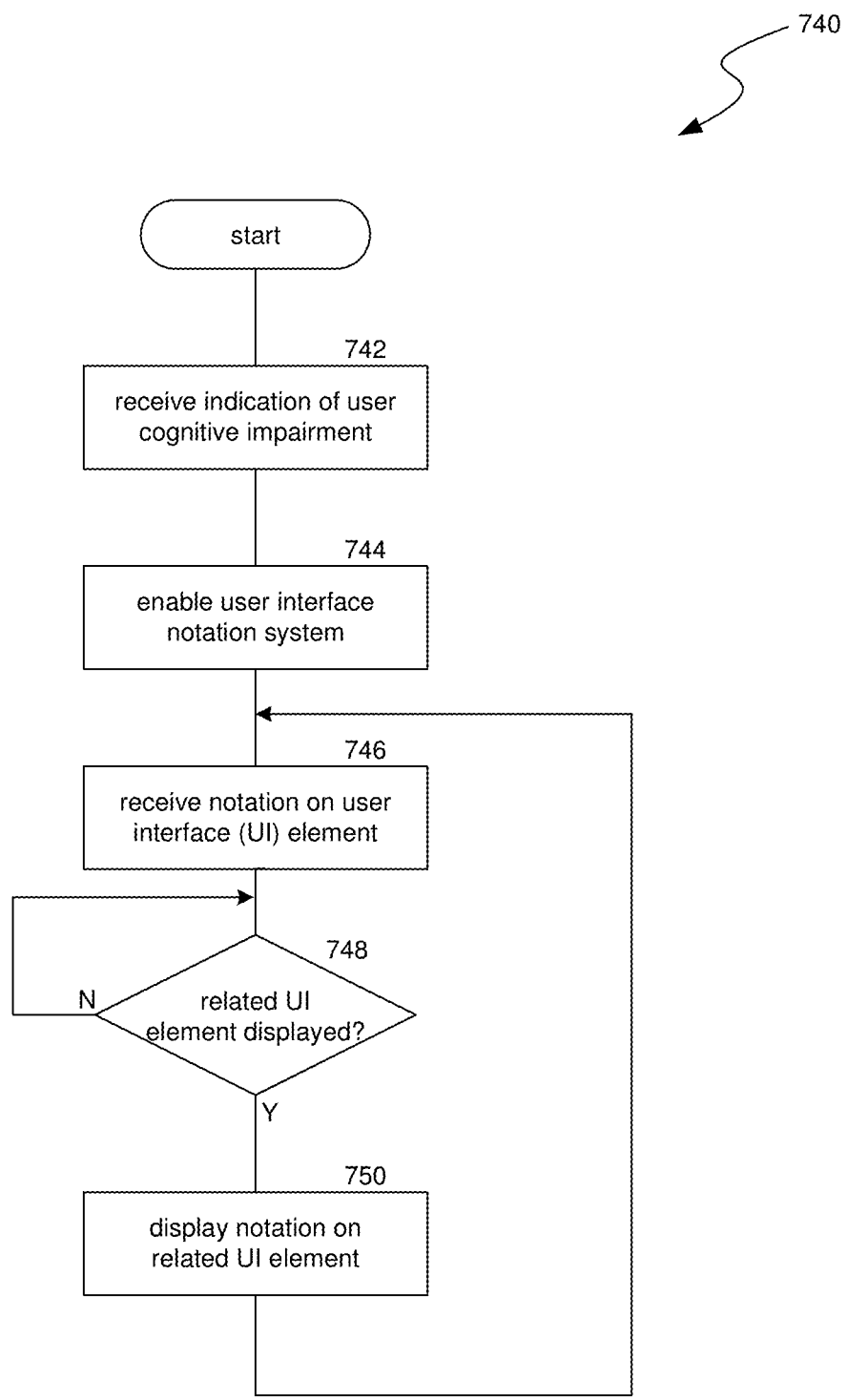

FIG. 7B is a flow diagram illustrating a process 740 used in some implementations for providing automated responses to identifications of users with cognitive impairment by establishing enhance memory procedures. In some cases, process 740 can be performed automatically following a cognitive impairment prediction made by the model produced by process 500 and/or following a validation of the cognitive impairment prediction made by process 600. In other cases, process 740 can be performed in response to a user command. In various implementations, process 740 can be performed on a server system, e.g., a server system hosting a website, providing data for an app, or serving a call center; or process 740 can be performed on a client system.

At block 742, process 740 can receive an indication that a current user has a cognitive impairment. This can be received as the output of the model produced by process 500, which may have been validated as not a false positive by process 600. In some implementations, the cognitive impairment prediction can include a prediction of a type of the cognitive impairment (e.g., dementia, brain injury, a learning disability, a stroke, post-traumatic stress disorder (PTSD), depression, schizophrenia, etc.) or sensory impact due to the cognitive impairment.

At block 744, process 740 can enable a user interface notation system. This system, through the operation of block 746-750, can provide the user options to set reminders for themselves in relation to particular content items (e.g., "I need to pay this bill every month," "I looked into this offer on date January 6th and decided not to accept it;" "I already made my annual donation to my charity"; etc.) Enabling the user interface notation system can include turning on controls or other capabilities that appear on every page of a website or within all features of an app, where the control allows the user to select a content item to which to add a notation (e.g., by dragging a "sticky note" from the control onto the content item).

At block 746, process 740 can receive a notation on a user interface (UI) element. For example, the user can click the control enabled at block 744 then click a UI element, providing a textual reminder; or can drag from the control onto the UI element followed by providing the textual or voice reminder, or use other haptic methods known to people familiar with the art. In some implementations, the notation can be provided through the user, e.g., typing, speaking, selecting from a set of pre-defined common notations, hand motions, etc.

At block 748, process 740 can determine when a UI element, related to the UI element on which a notation was made at block 746, is provided to the user. If so, at block 750, the notation is provided on the related UI element. Notably, this can be the original UI element on which the notation was made or a UI element that an administrator has specified as related to the original UI element; and/or the related UI element may be appearing in the same system (e.g., website, app, or call center interface) as the original UI element or may be appearing for the same user in a different system. As a first example, a user may have made a notation on a UI element on a website (e.g., a bill-pay interface), where that same UI shows up when the user visits that website again, the notation can be provided (reminding the user they already paid the bill). As a second example, a user may have made a notation on a UI element of a mobile device app (e.g., on a list of accounts), and when the user is accessing an automated call center that lists the user's accounts, the notation can be transcribed to audio and played for the user. As a third example, a user may have made a notation on a UI element of the app (e.g., a marketing notice for an insurance product), that marketing notice can have been mapped to a section of the app for that insurance product, thus when the user opens that section of the app, the notation is provided. As a fourth example, a user may have made a notation on a UI element of the website (e.g., on a user preferences page for email notifications), that setting can be mapped as related to future emails so when an email is sent to the user, the user's notation can be included.

While block 748 is shown as a loop, it can be implemented in other ways, such as a in a system where events associated with notations are registered with an event listener program, which causes block 750 to be performed when an event with a registered notation is detected. A version of blocks 748 and 750 can be performed concurrently for each notation received at block 746, and process 740 need not wait for blocks 748 and 750 to occur before enabling the user to provide a new notation at another iteration of block 746. Following block 750, process 700 can return to block 746 to receive another notation (or, though not shown, can return to block 748 to continue listening for an additional notation display event).

Figure 7C:
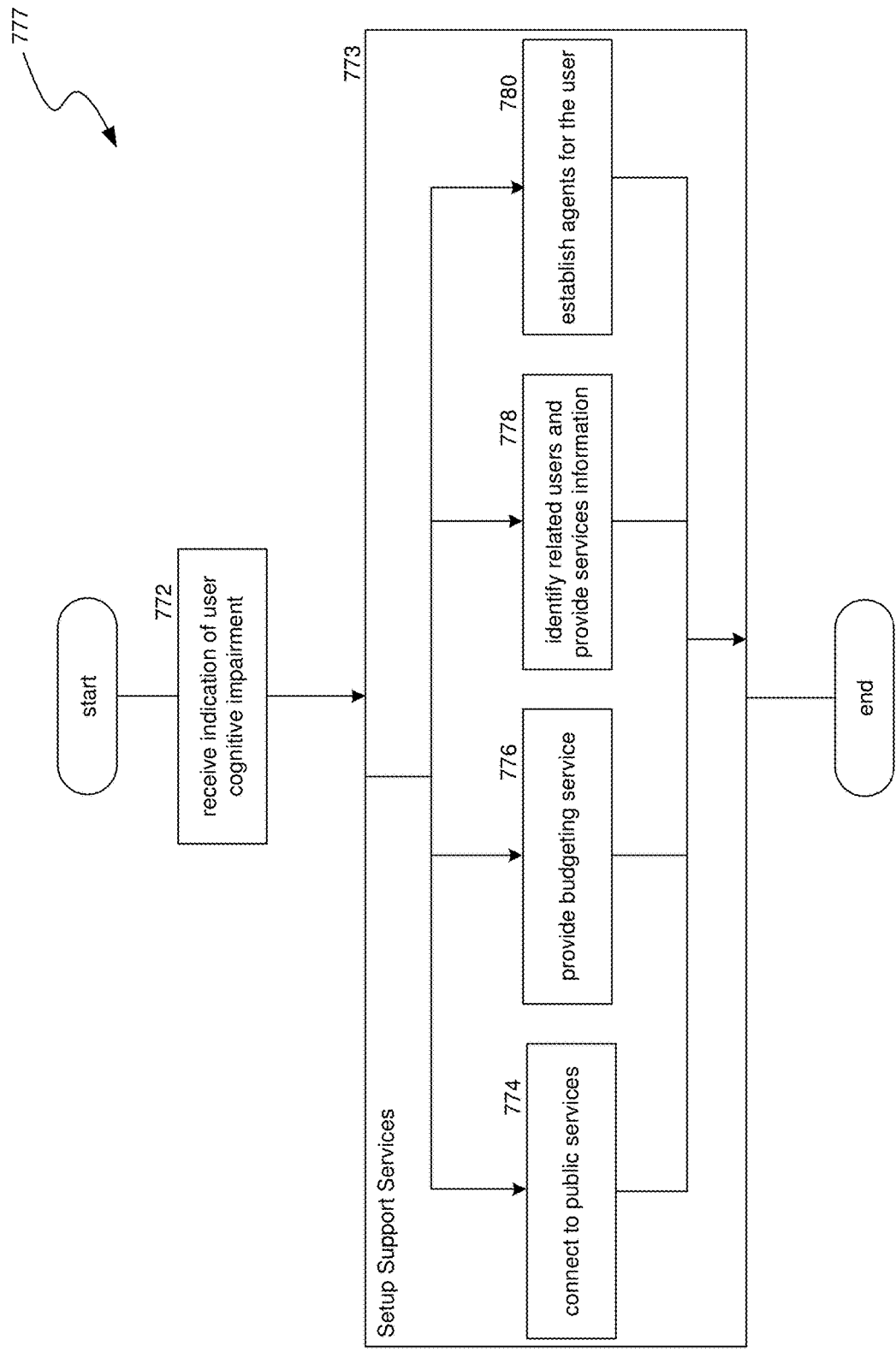

FIG. 7C is a flow diagram illustrating a process 770 used in some implementations for providing automated responses to identifications of users with cognitive impairment by automatically setting up support services for the user and/or for associated users. In some cases, process 770 can be performed automatically following a cognitive impairment prediction made by the model produced by process 500 and/or following a validation of the cognitive impairment prediction made by process 600. In other cases, process 770 can be performed in response to a user command. In various implementations, process 770 can be performed on a server system, e.g., a server system hosting a website, providing data for an app, or serving a call center; or process 770 can be performed on a client system.

At block 772, process 770 can receive an indication that a current user has a cognitive impairment. This can be received as the output of the model produced by process 500, which may have been validated as not a false positive by process 600. In some implementations, the cognitive impairment prediction can include a prediction of a type of the cognitive impairment (e.g., dementia, brain injury, a learning disability, a stroke, post-traumatic stress disorder (PTSD), depression, schizophrenia, etc.) as well as impact on senses, motor skills, etc.

At block 773, process 770 can take one or more actions through blocks 774-780 to help setup support services for the user or a related user. In various implementations, process 770 can perform one or more of blocks 774-780 while one or more of blocks 774-780 can be skipped.

At block 774, process 770 can setup connections for the user to public services. For example, different types of cognitive impairment can be mapped to information packets, website links, phone services, support groups, insurance packages, setup of in-person support, etc. Thus, depending on the type of cognitive impairment identified for the user, the information and/or support service can be automatically provided.

At block 776, process 770 can provide a budgeting service for the user. The budgeting service can include information on typical support and medical costs for the user's type of cognitive impairment. The budgeting service can then provide user interfaces and tools, looking at the user's known finances and insurance coverage, to set spending goals to help the user meet the expected financial challenges associated with the user's cognitive impairment type. An example of such a budgeting system is discussed below in relation to FIG. 11A.

At block 778, process 770 can identify users related to the user identified as having a cognitive impairment, such as family members. This identification can be based on pervious designations by the user, through shared accounts, through observed activities such as location history, etc. Similarly to block 774, block 778 can then automatically provide support services for people who have a family member dealing with a cognitive impairment (or a particular type of cognitive impairment). Examples of such support services include connecting the users to support groups, setting up counseling services, providing information packets such as what to expect the progression of the cognitive impairment to be or how to best setup the home to accommodate the cognitive impairment, offering heightened insurance services, etc. An example of such an information display is discussed below in relation to FIG. 11B.

At block 780, process 770 can establish agents for the user. In some implementations, this can include providing an interface for the user to establish another person as having power of attorney. In other cases, establishing an agent can include adding authorized users to bank accounts, insurance products, and other services so the other user can access the accounts and provide help to the user with cognitive impairment or can access the account if the user should become further incapacitated or die. In yet other cases, establishing an agent can include setting up an emergency contact and getting authorization to provide medical or other sensitive information to that person. In some implementations, establishing an agent can include establishing advance medical directives for the user prior to the cognitive impairment progressing past a point where such determinations can no longer be made. An example of such an agent setting system is discussed below in relation to FIG. 11C.

Following the execution of block 773, process 770 can end.

Figure 8:
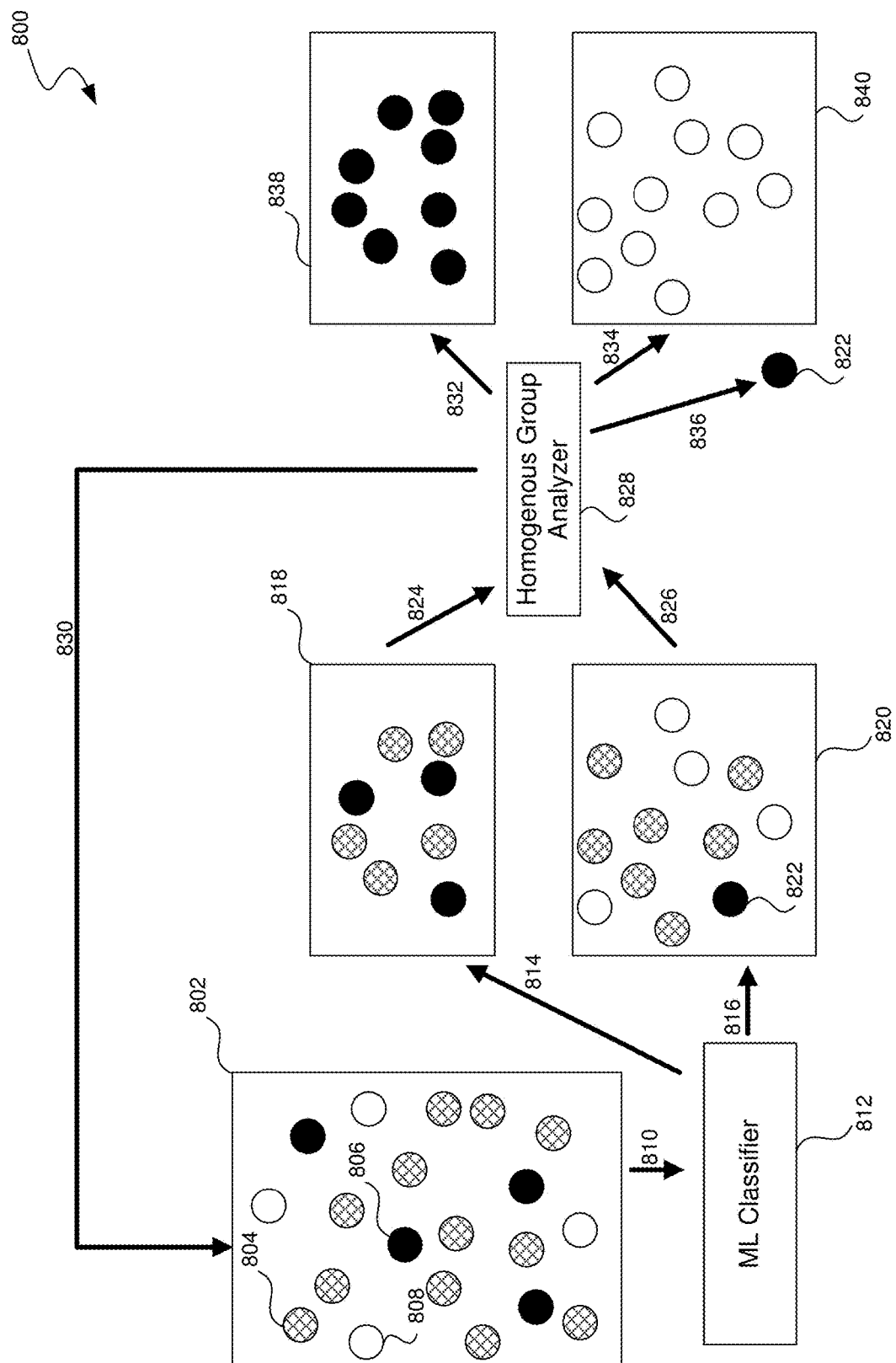
FIG. 8 is a conceptual diagram illustrating an example of applying an unsupervised machine learning user classification model to bootstrap cognitive impairment training data.

FIG. 8 is a conceptual diagram illustrating an example 800 of applying an unsupervised machine learning user classification model to bootstrap cognitive impairment training data. Example 800 starts with a classified training data set 802, which includes pre-classified cognitive impairment identified items in black—such as item 806; pre-classified non cognitive impairment identified items in white—such as item 808; and unclassified items in gray—such as item 804. At step 810, the training items are provided to ML classifier 812, which takes each item as input and attempts to sort them, at steps 814 and 816, into groups 818 and 820. In some cases, this process can be performed multiple times, each time adjusting parameters of the machine learning classifier 812, until the resulting groupings 818 and 820 do not change above a threshold amount between classification iterations (i.e., this is applying unsupervised learning techniques to classify the training items).

At steps 824 and 826, the resulting starting groups can be provided to homogenous group analyzer 828. Homogenous group analyzer 828 can determine whether the classifications by ML classifier 812 were generally correct by determining whether a threshold amount (e.g., 75%, 85%, or 90%) of the pre-classified cognitive impairment items ended up in the same group, and whether the threshold amount of the pre-classified non-cognitive impairment items ended up in the same group. Note, for example, all the cognitive impairment items (those shown as black) except item 822 are in group 818 and all the non-cognitive impairment items (those shown as white) are in group 820, satisfying the example threshold of 75% used in example 800. If the threshold had not been satisfied, example 800 would return, at step 830, to repeat the classification process, e.g., with different initial ML classifier parameters (using gradient descent), until the threshold is satisfied. Thus, in some implementations, the comparison of pre-classified elements to their resulting classification groups and potential model retraining can be a form of reinforcement learning.

Once the threshold is satisfied, at steps 836, pre-classified items that are in the wrong classification group, such as item 822, can be excluded from the training set or can be moved into the correct training set, based on their pre-classification. Finally, at step 832 and 834, previously unclassified items can be classified according to the cognitive impairment or non-cognitive impairment grouping they have been classified into. For example, previously unclassified items in group 818 can be classified as cognitive impairment items due to the threshold amount of pre-classified cognitive impairment items in group 818, creating group 838; and previously unclassified items in group 820 can be classified as non-cognitive impairment items due to the threshold amount of pre-classified non-cognitive impairment items in group 820, creating group 840.

Figure 9:
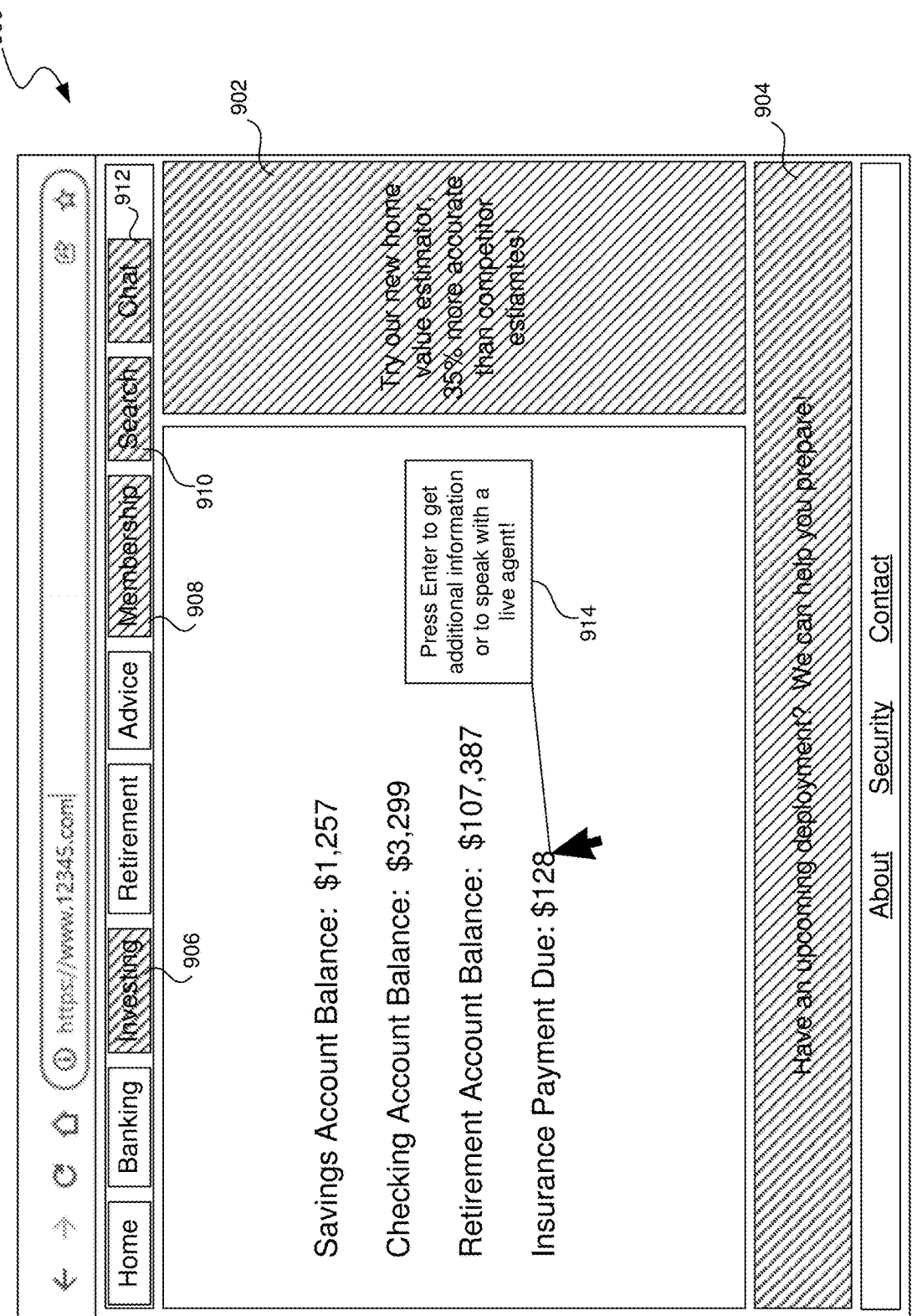
FIG. 9 is a conceptual diagram illustrating an example of automatically modifying computing system touchpoints based on a cognitive impairment determination.

FIG. 9 is a conceptual diagram illustrating an example 900 of automatically modifying computing system touchpoints based on a cognitive impairment determination. In example 900, a cognition analysis and response system has presented a website user interface (UI) for a user identified as having a cognitive impairment. Several items that would normally be included in this UI have been removed, as shown by greyed-out items 902-912. First, an administrator has classified some content items, such as side-bar 902, as for marketing purposes which may be confusing, and thus side-bar 902 has been removed. The administrator has also classified some content items, such as bottom-bar 904, as potentially triggering for a user with PTSD (which is the cognitive impairment identified for the current user in example 900), and thus bottom-bar 904 has been removed. In addition, the cognition analysis and response system has analyzed the current user's previous interactions with this UI and has determined that the user uses certain control elements, such as buttons 906-912, less than a threshold amount (e.g., no more than twice each or less than 2% of the times these UI elements are presented). In response to the cognitive impairment determination for the current user and these determinations of these being limited use content items, buttons 906-912 have been removed. Another possible change is enacting a function that audibly "reads" certain content to the user, as well as visually highlighting the content as it is "read" to the user.

Also in example 900, enhanced help features have been enabled in the UI in response to the determination that the current user has a cognitive impairment. As the user move her mouse over various UI elements, additional help options are provided. For example, block 914 has been shown in response to the user moving her mouse over the "Insurance Payment Due" content item, which instructs the user to press enter to open a widget though which additional information for that content item can be provide and/or through which a customer service representative can be reached (e.g., providing the customer service representative an indication of which content item the user was interacting with for her inquiry).

Figure 10:
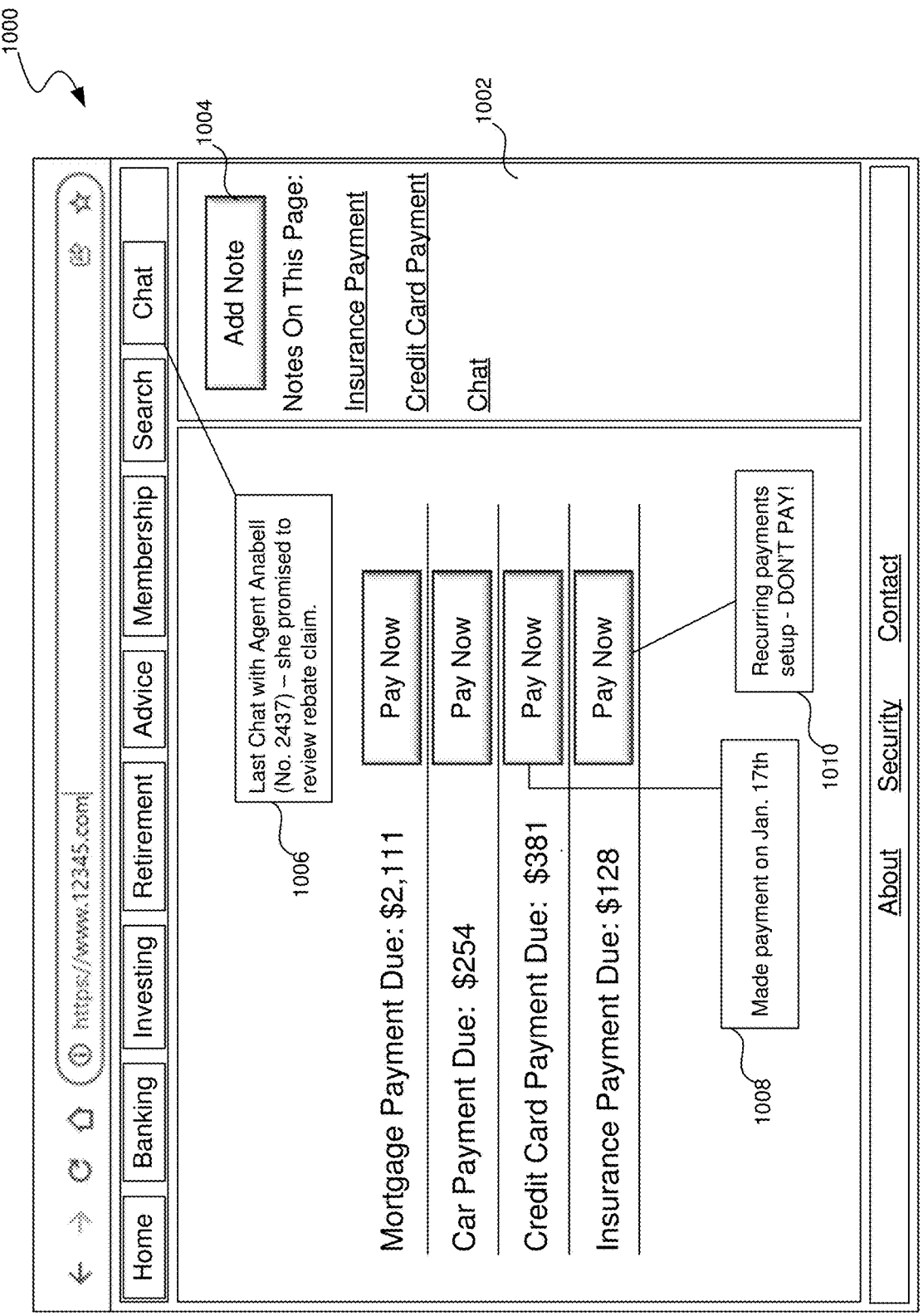
FIG. 10 is a conceptual diagram illustrating an example of a system for adding persistent notes to UI elements for users determined to have a cognitive impairment.

FIG. 10 is a conceptual diagram illustrating an example 1000 of a system for adding persistent notes to UI elements for users determined to have a cognitive impairment. In example 1000, a cognition analysis and response system has presented a website user interface (UI) for a user identified as having a cognitive impairment, with an extra widget 1002 for adding notes to UI elements. Widget 1002 has a button 1004 for enabling a next click to add a new note and a list of notes already added to the current UI. The user has added a note 1006 to the chat button, reminding herself of the results of a last call with a customer service representative; has added a note 1008 reminding herself that she already made a payment for this card on January 17th and therefore does not need to make another one; and has made a note 1010, reminding herself that she setup recurring payments for her insurance and therefore does not need to make manual payments. Each of these notes can be presented the next time the user sees these UI elements. In some cases, these notes show up when the page is loaded, while in other cases the UI elements have a note indicator added to them and the full note shows up when the user selects the UI element (e.g., by tapping it or moving her mouse over it).

In some implementations, when a note is added to a UI element, that note can persist and be presented when related UI elements are shown. For example, the note 1008 about having made a credit card payment can be presented in an app that has a related tool for paying the same credit card. As another example, the note 1006 about a previous chat with a customer service representative can be shown to a customer service representative the next time this user calls into a call center.

Figure 11A:
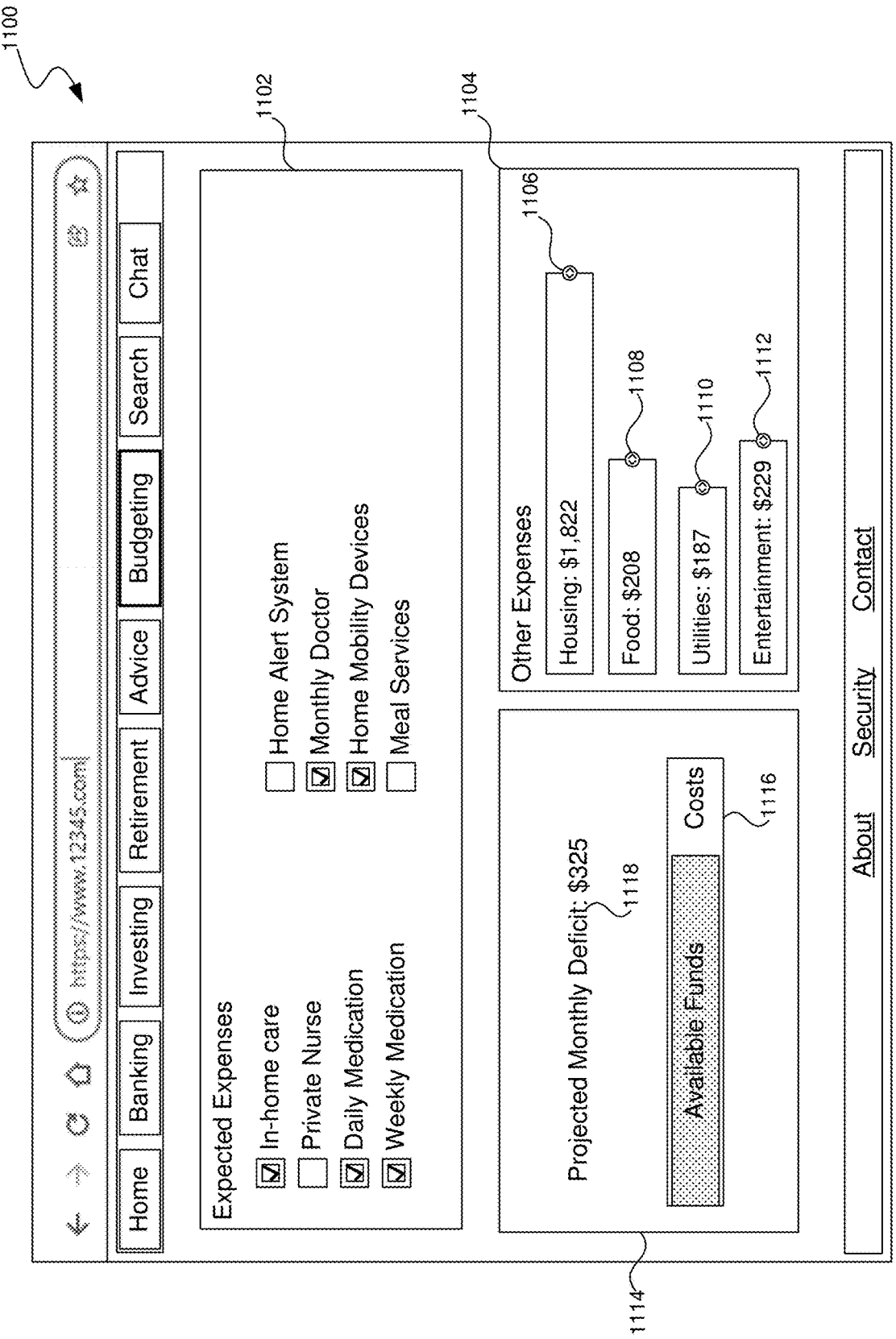
FIG. 11A is a conceptual diagram illustrating an example of a budgeting service provided for users determined to have a cognitive impairment.

FIG. 11A is a conceptual diagram illustrating an example 1100 of a budgeting service provided for users determined to have a cognitive impairment. In example 1100, the budgeting services includes three elements, a cost selector 1102, an expense modifier 1104, and a projection 1114. The cost selector 1102 can provide a list of costs determined to be associated with cognitive impairment. In some implementations, the list of costs can be specific to the type of cognitive impairment identified for the current user. In some implementations, the cognition analysis and response system can pre-check (in cost selector 1102) a set of these costs that are most often incurred by users with cognitive impairment or with the type of cognitive impairment identified for the current user. For example, the cognition analysis and response system can identify purchases made (e.g., through financial accounts the cognition analysis and response system can access) by other users with cognitive impairment or with that particular type of cognitive impairment and, using a statistical analysis, determine those most likely to be incurred by the current user. Upon reaching the budgeting system shown in example 1100, the user can check or un-check options she thinks she is mostly like to use. In some implementations, additional controls are provided in cost selector 1102—such as to set specific amounts the user expects to be associated with that cost (overriding a default amount set for that cost). In some implementations, the cognition analysis and response system can interface with the user's insurance system, allowing the cognition analysis and response system to determine costs for the current user—e.g., amounts not covered by her health insurance, factoring in co-pays, etc.

The expense modifier 1104 can estimate the current user's expenditures in various categories such as housing, food, utilities, entertainment, etc. These estimations can be based on the cognition analysis and response system's access to the current user's financial accounts such as checking, savings, and credit cards, e.g., the cognition analysis and response system can categorize various expenditures from these accounts and can determine monthly averages for each category. The user can then estimate how much she can cut back in categories, adjusting the category amounts by manipulating controls 1106-1112. For example, a user may determine that moving to a less expensive apartment would be a good way to save money, and may thus drag control 1106 to the left, to reduce her expected housing costs.

The projection 1114 can include a comparison 1116 showing the amount of funds the user is expected to have as compared to the expected costs of the user. The funds can be determined for a period (e.g., monthly) and can be based on the cognition analysis and response system's access to the current user's financial accounts such as checking, savings, investments, etc.—with the cognition analysis and response system viewing past deposits and increases in these accounts to estimate an overall income. The expected costs can be based on a combination of the costs set in cost selector 1102 (either default amounts or user-selected amounts for each selected cost) and expense modifier 1104 (with the amounts totaled across the expense categories). The projection 1114 can also include an overall amount 1118, showing the user how her funds are above or below her current projected total costs.

FIG. 11B is a conceptual diagram illustrating an example 1140 of information sources for users identified to be related to a user determined to have a cognitive impairment. Example 1140 includes an information pane 1142 with various categories of information. As shown by the header 1144, the information items selected for display can include items selected for a particular type of cognitive impairment (in this case stroke) and for users with a particular relationship to the user for whom that type of cognitive impairment was identified (in this example spouses). The cognition analysis and response system can include manual mappings of such information items to cognitive impairment types and relationship types. Examples of the categories of information items that can be provided are support groups 1146, counseling services 1148, information packets 1150, and insurance services 1152. Each information item in each category can include a set of data, such as a title, schedule, additional information link, and/or download link.

Figure 11C:
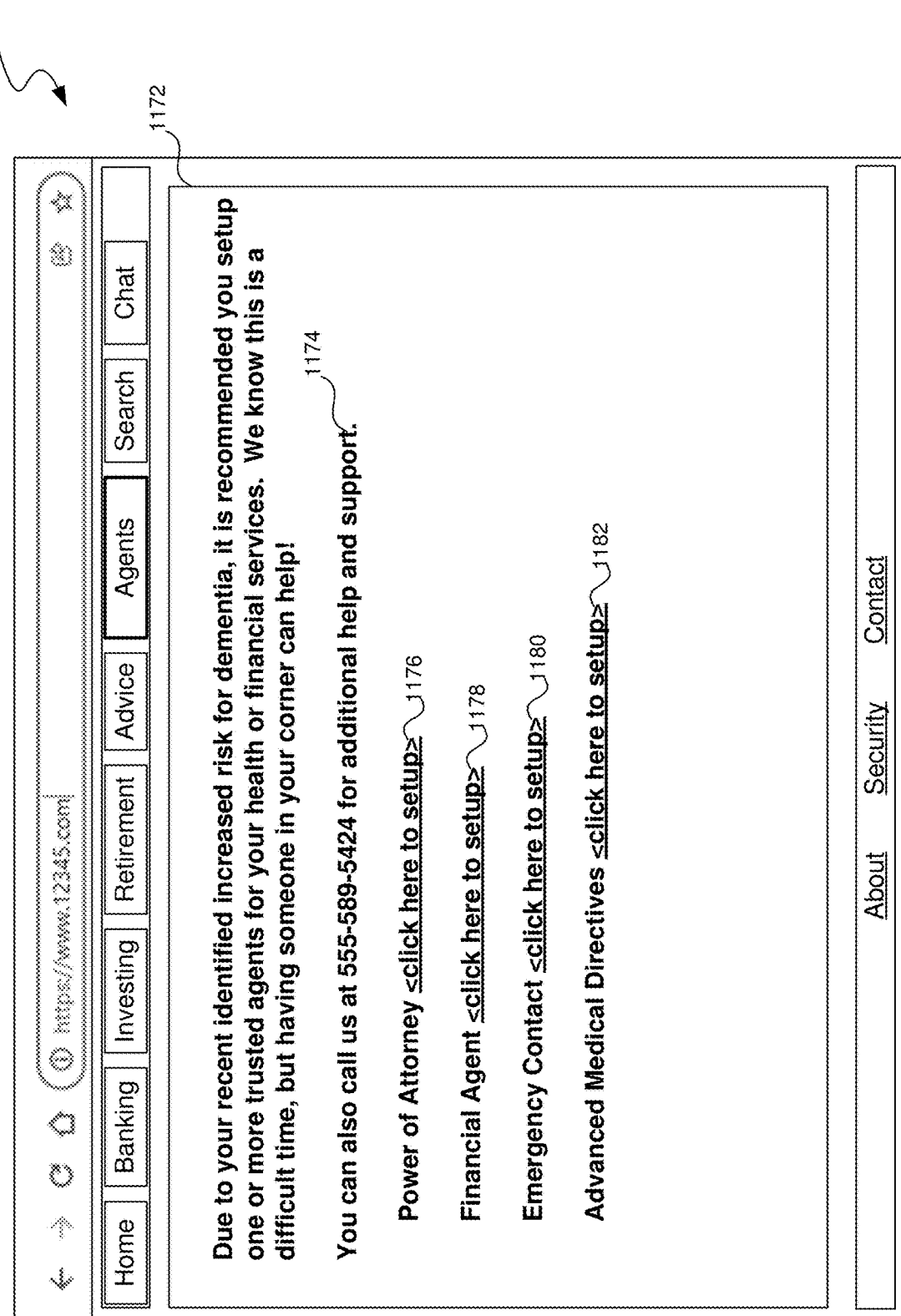
FIG. 11C is a conceptual diagram illustrating an example of an agent and advanced directive setup service for users determined to have a cognitive impairment.

FIG. 11C is a conceptual diagram illustrating an example 1170 of an agent and advanced directive setup service for users determined to have a cognitive impairment. Example 1170 includes an agent setting top-level panel 1172 with instructions, a message 1174 offering live support, and access to tools 1176-1182 to setup various types of agents and advanced directives.

The power of attorney tool 1176 can guide the user through a process for establishing a power of attorney, such as by providing appropriate forms and advising on the legal process to execute them, such as by informing the user on the notarization and witness requirements in the state in which the user lives. In some implementations, the power of attorney tool 1176 can also provide access to attorneys to help the user complete this process and/or communication tools for informing and executing documents with the user designated to have the power of attorney.

The financial agent tool 1178 can provide widgets for the user to establish a financial agent that has access to one or more of the user's financial accounts. This can be total access to perform any action the user can perform or limited access, e.g., to perform actions following certain proofs—such as showing a doctor's verification of incapacitation of the user or a death certificate; and this can be limited actions such as viewing accounts but only making transfers to designated beneficiaries or trustees. In various implementations, the financial agent tool 1178 can provide online forms and/or communication methods to complete these financial agent designations and communicate with users having such designations.

The emergency contact tool 1180 can provide forms and communication tools for establishing an emergency contact. Through emergency contact tool 1180, the user can designate who is to be an emergency contact, what triggers contacting each emergency contact, and what decision making powers are to be granted that emergency contact in a given situation. The user can also select in which systems the emergency contacts are to be designated. For example, the cognition analysis and response system can have been provisioned with access for the user to various institutions and financial accounts and can have procedures to set emergency contacts for each.

The advanced medical directives tool 1182 can guide the user through a process for establishing an advanced medical directive, such as by providing appropriate forms and advising on the legal process to execute them, such as by informing the user on the notarization and witness requirements in the state in which the user lives. In some implementations, the advanced medical directives tool 1182 can also provide access to attorneys to help the user complete this process and/or interfaces for distributing these advanced medical directives to the appropriate medical providers and/or family members (or other established agents/emergency contacts).

Several implementations of the disclosed technology are described above in reference to the figures. The computing devices on which the described technology may be implemented can include one or more central processing units, memory, input devices (e.g., keyboard and pointing devices), output devices (e.g., display devices), storage devices (e.g., disk drives), and network devices (e.g., network interfaces). The memory and storage devices are computer-readable storage media that can store instructions that implement at least portions of the described technology. In addition, the data structures and message structures can be stored or transmitted via a data transmission medium, such as a signal on a communications link. Various communications links can be used, such as the Internet, a local area network, a wide area network, or a point-to-point dial-up connection. Thus, computer-readable media can comprise computer-readable storage media (e.g., "non-transitory" media) and computer-readable transmission media.

Reference in this specification to "implementations" (e.g., "some implementations," "various implementations," "one implementation," "an implementation," etc.) means that a particular feature, structure, or characteristic described in connection with the implementation is included in at least one implementation of the disclosure. The appearances of these phrases in various places in the specification are not necessarily all referring to the same implementation, nor are separate or alternative implementations mutually exclusive of other implementations. Moreover, various features are described which may be exhibited by some implementations and not by others. Similarly, various requirements are described which may be requirements for some implementations but not for other implementations.

As used herein, being above a threshold means that a value for an item under comparison is above a specified other value, that an item under comparison is among a certain specified number of items with the largest value, or that an item under comparison has a value within a specified top percentage value. As used herein, being below a threshold means that a value for an item under comparison is below a specified other value, that an item under comparison is among a certain specified number of items with the smallest value, or that an item under comparison has a value within a specified bottom percentage value. As used herein, being within a threshold means that a value for an item under comparison is between two specified other values, that an item under comparison is among a middle specified number of items, or that an item under comparison has a value within a middle specified percentage range. Relative terms, such as high or unimportant, when not otherwise defined, can be understood as assigning a value and determining how that value compares to an established threshold. For example, the phrase "selecting a fast connection" can be understood to mean selecting a connection that has a value assigned corresponding to its connection speed that is above a threshold.

As used herein, the word "or" refers to any possible permutation of a set of items. For example, the phrase "A, B, or C" refers to at least one of A, B, C, or any combination thereof, such as any of: A; B; C; A and B; A and C; B and C; A, B, and C; or multiple of any item such as A and A; B, B, and C; A, A, B, C, and C; etc.

Although the subject matter has been described in language specific to structural features and/or methodological acts, it is to be understood that the subject matter defined in the appended claims is not necessarily limited to the specific features or acts described above. Specific embodiments and implementations have been described herein for purposes of illustration, but various modifications can be made without deviating from the scope of the embodiments and implementations. The specific features and acts described above are disclosed as example forms of implementing the claims that follow. Accordingly, the embodiments and implementations are not limited except as by the appended claims.

Any patents, patent applications, and other references noted above are incorporated herein by reference. Aspects can be modified, if necessary, to employ the systems, functions, and concepts of the various references described above to provide yet further implementations. If statements or subject matter in a document incorporated by reference conflicts with statements or subject matter of this application, then this application shall control.

We claim:

1. A method for detecting cognitive impairment in users of a computing system, the method comprising:
    obtaining multiple sets of inputs, each associated with a different user, of multiple users, and each set of inputs, of the multiple sets of inputs, having multiple dimensions, wherein the multiple dimensions include:
    transaction history inputs, and
    computer user interface (UI) interaction pattern inputs;
    labeling multiple of the users associated with the sets of inputs as either having or not having a cognitive impairment by applying an unsupervised learning classifier to the sets of inputs;
    training a machine learning model to identify users with cognitive impairments through a supervised learning process that iterates through the multiple sets of inputs, each set of inputs being associated with one different user, of the multiple users, and each different user being assigned a label as either having or not having a cognitive impairment, wherein each iteration includes updating aspects of the machine learning model by:
    applying the machine learning model to a current set of inputs, of the multiple sets of inputs, for a current iteration to produce results by taking the current set of inputs through one or more nodes, each node:
    transforming an input, of the current set of inputs, according to a node coefficient, and passing the results, with a particular edge weight, to a next layer until the results are mapped to a cognitive impairment prediction result;
    comparing the cognitive impairment prediction result to the label assigned to the different user associated with the current set of inputs; and
    updating the machine learning model by updating the node coefficient and/or the particular edge weight of at least one node, of the one or more nodes, based on the comparison;
    labeling a new user as having a cognitive impairment based on an application of the trained machine learning model to a new set of inputs corresponding to the new user, the new set of inputs including one or more interactions of the user with a keyboard, of a computing system, as an input device,
    wherein the labeled cognitive impairment is at least one of a brain injury, a learning disability, a stroke, post-traumatic stress disorder, depression, schizophrenia, or any combination thereof; and based on the labeling of the new user as having the cognitive impairment, applying one or more adaptive measures to the computing system, the one or more adaptive measures including automatically switching, by the computing system, to a microphone as the input device of the computing system, through which one or more further interactions of the user are received.

2. The method of claim 1, wherein the applying the unsupervised learning classifier to the sets of inputs includes:
- iteratively applying the unsupervised learning classifier,
- wherein each iteration includes applying the unsupervised learning classifier to each of the sets of inputs to get a classification, and
- wherein the iterations end when the classifications between iterations do not vary above a threshold amount.

3. The method of claim 2,
- wherein at least some of the multiple sets of inputs are each associated with one different user who has a pre-classification of having or not having a cognitive impairment; and
- wherein the applying the unsupervised learning classifier to the sets of inputs further includes:
- analyzing, for the inputs with pre-classifications, ratios of correctly classified inputs to incorrectly classified inputs in each of multiple clusters of classifications resulting when the classification iterations end;
- based on the analyzing, re-performing the classification iterations with different ones of the multiple dimensions until the ratios of correctly classified inputs to incorrectly classified inputs in each of the multiple clusters are above a threshold level of cluster homogeneousness; and
- in response to the ratios being above the threshold level of cluster homogeneousness, performing the labeling of the multiple of the users associated with the sets of inputs by labeling each different user in a cluster with the pre-classification most prevalent in that cluster.

4. The method of claim 1, wherein the multiple dimensions further include communication history inputs and errors or lost data history inputs, and wherein the applying the machine learning model to the current set of inputs includes one or more of:
- formulating the communication history inputs as codes corresponding to identified emotional state changes, language structure changes, word choice changes, or any combination thereof;
- formulating the transaction history inputs as one or more values representing a number of late payments, a number of repeated payments, or ratios of recent late payments or repeated payments to a previous amount of late payments or repeated payments for the one different user, of the multiple users, or for a typical user;
- formulating the errors or lost data history inputs as one or more values indicating a frequency of such losses as compared to a previous loss rate for the one different user, of the multiple users, or for a typical user; or
- any combination thereof.

5. The method of claim 1, wherein the multiple dimensions further include location or body state history inputs, and wherein the applying the machine learning model to the current set of inputs includes one or more of:
- formulating the location or body state history inputs as a frequency of identified abnormalities in recorded location or body state for the one different user of the multiple users;
- formulating the computer user interface (UI) interaction pattern inputs as a frequency of identified abnormalities in UI interactions performed by the one different user of the multiple users; or
- any combination thereof.

6. The method of claim 1,
- wherein the machine learning model is a type of a neural network; and
- wherein the updating the machine learning model, based on the comparison, includes applying a loss function to update parameters of the neural network such that the cognitive impairment prediction result is closer to the label assigned to the one different user associated with the current set of inputs.

7. The method of claim 1,
- wherein the machine learning model is trained to identify types of cognitive impairment; and
- wherein the labeling the new user as having the cognitive impairment includes labeling the new user with a type of cognitive impairment indicated by the machine learning model.

8. A non-transitory computer-readable storage medium storing instructions that, when executed by a computing system, cause the computing system to perform a process for detecting cognitive impairment in users, the process comprising:
- obtaining multiple sets of inputs, each associated with a different user, of multiple users, and each set of inputs, of the multiple sets of inputs, having multiple dimensions;
- labeling multiple of the users associated with the sets of inputs as either having or not having a cognitive impairment by iteratively applying an unsupervised learning classifier to the set of inputs,
- wherein each iteration includes applying the unsupervised learning classifier to each of the sets of inputs to get a classification, and
- wherein the iterations end when the classifications between iterations do not vary above a threshold amount;
- training a machine learning model to identify users with cognitive impairments through a supervised learning process that iterates through the multiple sets of inputs, each set of inputs being associated with one different user, of the multiple users, and each different user being assigned a label as either having or not having a cognitive impairment, wherein each iteration includes updating aspects of the machine learning model by:
- applying the machine learning model to a current set of inputs, of the multiple sets of inputs, for a current iteration to produce results by taking the current set of inputs through one or more nodes, each node:
- transforming an input, of the current set of inputs, according to a node coefficient, and passing the results, with a particular edge weight, to a next layer until the results are mapped to a cognitive impairment prediction result;
- comparing the cognitive impairment prediction result to the label assigned to the different user associated with the current set of inputs; and
- updating the machine learning model by updating the node coefficient and/or the particular edge weight of at least one node, of the one or more nodes, based on the comparison;
- labeling a new user as having a cognitive impairment based on an application of the trained machine learning model to a new set of inputs corresponding to the new user, the new set of inputs including one or more interactions of the user with a keyboard, of a computing device, as an input device, wherein the labeled cognitive impairment is at least one of a brain injury, a learning disability, a stroke, post-traumatic stress disorder, depression, schizophrenia, or any combination thereof; and based on the labeling of the new user as having the cognitive impairment, applying one or more adaptive measures to the computing system, the one or more adaptive measures including automatically switching, by the computing device, to a microphone as the input device of the computing device, through which one or more further interactions of the user are received.

9. The non-transitory computer-readable storage medium of claim 8, wherein at least some of the multiple sets of inputs are each associated with one different user, of the multiple users, who has a pre-classification of having or not having a cognitive impairment; and wherein the applying the unsupervised learning classifier to the sets of inputs further includes:

analyzing, for the inputs with pre-classifications, ratios of correctly classified inputs to incorrectly classified inputs in each of multiple clusters of classifications resulting when the classification iterations end;

based on the analyzing, re-performing a set of classification iterations with different ones of the multiple dimensions until the ratios of correctly classified inputs to incorrectly classified inputs in each of the multiple clusters are above a threshold level of cluster homogeneousness; and in response to the ratios being above the threshold level of cluster homogeneousness, performing the labeling of the multiple of the users associated with the sets of inputs by labeling each user in a cluster with the pre-classification most prevalent in that cluster.

10. The non-transitory computer-readable storage medium of claim 8, wherein the applying the machine learning model to the current set of inputs includes one or more of:

formulating the location or body state history inputs as a frequency of identified abnormalities in recorded location or body state for the one different user of the multiple users;

formulating the computer user interface (UI) interaction pattern inputs as a frequency of identified abnormalities in UI interactions performed by the one different user of the multiple users; or any combination thereof.

11. The non-transitory computer-readable storage medium of claim 8, wherein the machine learning model is a type of a neural network; and wherein the updating the machine learning model, based on the comparison, includes applying a loss function to update parameters of the neural network.

12. A computing system for detecting cognitive impairment in users, the computing system comprising:

one or more processors; and one or more memories storing instructions that, when executed by the one or more processors, cause the computing system to perform a process comprising:

obtaining multiple sets of inputs, each associated with a different user, of multiple users, and each set of inputs, of the multiple sets of inputs, having multiple dimensions;

labeling multiple of the users associated with the sets of inputs as either having or not having a cognitive impairment by applying an unsupervised learning classifier to the set of inputs;

training a machine learning model to identify users with cognitive impairments through a supervised learning process that updates aspects of the machine learning model using the ones of the multiple sets of inputs that are associated with one different user, of the multiple users, who has been labeled as either having or not having a cognitive impairment, by performing multiple iterations, wherein the machine learning model is a type of neural network, wherein each iteration includes updating aspects of the machine learning model by:

applying the machine learning model to a current set of inputs, of the multiple sets of inputs, for a current iteration to produce results by taking the current set of inputs through one or more nodes, each node:

transforming an input, of the current set of inputs, according to a node coefficient, and passing the results, with a particular edge weight, to a next layer until the results are mapped to a cognitive impairment prediction result;

comparing the cognitive impairment prediction result to the label assigned to the different user associated with the current set of inputs; and updating the machine learning model by:

updating the node coefficient and/or the particular edge weight of at least one node, of the one or more nodes, based on the comparison; and applying a loss function to update parameters of the neural network such that the cognitive impairment prediction result is closer to the label assigned to the one different user associated with the current set of inputs;

labeling a new user as having a cognitive impairment based on an application of the trained machine learning model to a new set of inputs corresponding to the new user, the new set of inputs including one or more interactions of the user with a keyboard, of a computing device, as an input device, wherein the labeled cognitive impairment is at least one of a brain injury, a learning disability, a stroke, post-traumatic stress disorder, depression, schizophrenia, or any combination thereof; and based on the labeling of the new user as having the cognitive impairment, applying one or more adaptive measures to the computing device, the one or more adaptive measures including automatically switching, by the computing device, to a microphone as the input device of the computing device, through which one or more further interactions of the user.

13. The computing system of claim 12, wherein at least some of the multiple sets of inputs are each associated with one different user who has a pre-classification of having or not having a cognitive impairment; and wherein the applying the unsupervised learning classifier to the sets of inputs further includes:

analyzing, for the inputs with pre-classifications, ratios of correctly classified inputs to incorrectly classified inputs in each of multiple clusters of classifications resulting when the classification iterations end;

based on the analyzing, re-performing a set of classification iterations with different ones of the multiple dimensions until the ratios of correctly classified inputs to incorrectly classified inputs in each of the multiple clusters are above a threshold level of cluster homogeneousness; and in response to the ratios being above the threshold level of cluster homogeneousness, performing the labeling of the multiple of the users associated with the sets of inputs by labeling each user in a cluster with the pre-classification most prevalent in that cluster.

14. The method of claim 1, wherein one or more iterations further include:

identifying a false positive or a false negative cognitive impairment determination result; and excluding the current set of inputs from further training of the machine learning model.

15. The method of claim 14, wherein the false positive or the false negative cognitive impairment determination result is identified by one or both of:

comparing a confidence value, generated by the machine learning model, to a threshold value; and/or comparing a progression of the cognitive impairment determination result, over multiple iterations, to one or more historical patterns of cognitive impairment progression.

16. The method of claim 1, further comprising:

wherein the one or more automated adaptive measures further include updating a user interface for the new user.

17. The method of claim 1, wherein the computer UI interaction pattern inputs include user interactions, with a user device, shown on a display of the user device.

18. The method of claim 1, wherein the one or more adaptive measures includes at least one of:

disabling user interfaces and functionality tagged as being complicated or dense, adjusting criteria for recognition of haptic motions, enabling simpler user interfaces, or any combination thereof.

* * * * *